US007771952B2

(12) United States Patent
Strittmatter et al.

(10) Patent No.: US 7,771,952 B2
(45) Date of Patent: Aug. 10, 2010

(54) MODULATORS AND MODULATION OF THE INTERACTION BETWEEN RGM AND NEOGENIN

(75) Inventors: Stephen Strittmatter, Guilford, CT (US); Bernhard Mueller, Neustadt (DE); Lutz Deitinghoff, Ludwigshafen (DE)

(73) Assignee: Abott Laboratories, Abbott Park, IL (US)

( * ) Notice: Subject to any disclaimer, the term of this patent is extended or adjusted under 35 U.S.C. 154(b) by 24 days.

(21) Appl. No.: 10/519,132

(22) PCT Filed: Jun. 26, 2003

(86) PCT No.: PCT/US03/20147

§ 371 (c)(1),
(2), (4) Date: Sep. 14, 2005

(87) PCT Pub. No.: WO2004/003150

PCT Pub. Date: Jan. 8, 2004

(65) Prior Publication Data

US 2006/0252101 A1 Nov. 9, 2006

Related U.S. Application Data

(60) Provisional application No. 60/392,062, filed on Jun. 26, 2002.

(51) Int. Cl.
*G01N 33/53* (2006.01)
*C07K 14/00* (2006.01)
*C07K 16/00* (2006.01)
*A61K 35/30* (2006.01)

(52) U.S. Cl. .................... 435/7.1; 530/350; 530/387.1; 530/839; 424/570

(58) Field of Classification Search ....................... None
See application file for complete search history.

(56) References Cited

U.S. PATENT DOCUMENTS

| | | | | |
|---|---|---|---|---|
| 4,946,778 | A | 8/1990 | Ladner et al. | 435/69.6 |
| 5,525,490 | A | 6/1996 | Erickson et al. | 435/29 |
| 5,541,109 | A | 7/1996 | Searfoss, III et al. | 435/252.3 |
| 5,747,262 | A | 5/1998 | Hinck et al. | 435/7.1 |
| 6,004,746 | A | 12/1999 | Brent et al. | 435/6 |
| 6,087,326 | A | 7/2000 | Hinck et al. | 514/2 |

FOREIGN PATENT DOCUMENTS

| | | |
|---|---|---|
| EP | 0 321 201 A2 | 6/1989 |
| EP | 0 360 257 A2 | 3/1990 |
| EP | 0 291 533 | 10/1995 |
| WO | WO 94/29469 | 12/1994 |
| WO | WO 97/00957 | 1/1997 |
| WO | WO 98/25947 | 6/1998 |
| WO | WO 99/51741 | 10/1999 |
| WO | WO 00/02911 | 1/2000 |
| WO | WO 00/05410 | 2/2000 |
| WO | WO 00/14271 | 3/2000 |
| WO | WO 00/17221 | 3/2000 |
| WO | WO 02/051438 A2 | 7/2002 |

OTHER PUBLICATIONS

Yamashita et al. Curr Opin Neurobiol 17: 29-34, 2007.*
Matsunaga et al. Dev Gr Diff 46: 481-486, 2004.*
Rajagopalan et al. Nat Cell Biol 6: 756-762, 2004.*
Niederkofler et al. J Neurosc 24: 808-818, 2004.*
Wells, 1990, Biochemistry 29:8509-8517.*
Ngo et al., 1994, the Protein Folding Problem and Tertiary Structure Prediction, pp. 492-495.*
Bork, 2000, Genome Research 10:398-400.*
Skolnick et al., 2000, Trends in Biotech. 18(1):34-39, especially p. 36 at Box 2.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Accession No. BC23870 (Feb. 24, 2004).
Accession No. AK080819 (Apr. 3, 2004).
Accession No. BC022603 (Jan. 3, 2005).
Accession No. BI818609 (Oct. 4, 2001).
Accession No. BI769500 (Sep. 25, 2001).
Anderson *Science*, 256:808-813 (1992).
Bagnard et al. *Development*, 125:5043-5053 (1998).
Blömer et al. *J. Virol*., 71(9):6641-6649 (1997).
Bonhoeffer et al. *Trends Neurosci*., 7:378-381 (1984).
Caroni et al. *Neuron*, 1:85-96 (1988).
Caroni et al. *J. Cell Biol*., 106:1281-1288 (1988).
Charron et al. *J. Biol. Chem*., 270(43):25739-25745 (1995).
Chen et al. *Nature*, 403:434-439 (2000).
Cheng et al. *Cell*, 79(1):157-168 (1994).
Cox et al. *Neuron*, 2(1):31-37 (1990).
David et al. *Science*, 214:931-933 (1981).
Davis et al. *Science*, 266:816-819 (1994).
Drescher et al. *Cell*, 82(3):359-370 (1995).
Famulok et al. *Curr. Op. Chem. Biol*., 2:320-327 (1998).
Fazeli et al. *Nature*, 386:796-804 (1997).
Feldheim et al. *Neuron*, 21(6):1303-1313 (1998).
Feldheim et al. *Neuron*, 25(3):563-574 (2000).
Flanagan et al. *Annu. Rev. Neurosci*., 21:309-345 (1998).
Fournier et al. *Nature*, 409:341-346 (2001).

(Continued)

*Primary Examiner*—Jeffrey Stucker
*Assistant Examiner*—Aditi Dutt
(74) *Attorney, Agent, or Firm*—Sreenivasarao Vepachedu

(57) ABSTRACT

This invention relates to drug screening using mammalian repulsive guidance molecules and mammalian Neogenin. In addition, the invention provides for methods of preventing, alleviating or treating various disorders of the nervous system, angiogenic disorders or disorders of the cardio-vascular system and malignancies of different etiology by disrupting the interaction between RGM and Neogenin.

2 Claims, 10 Drawing Sheets

OTHER PUBLICATIONS

Geddes et al. *Nat. Med.*, 3(12):1402-1404 (1997).
Geddes et al. *Front Neuroendocrinol.*, 20(4):296-316 (1999).
Geisbrecht et al. *J. Biol. Chem.*, 278(35):32561-32568 (2003).
GenBank NT_039474 (Aug. 31, 2004).
Genbank NM_008684 (Feb. 28, 2005).
Gierer *Development*, 101(3):479-489 (1987).
Giordano et al. *Nat. Med.*, 2(5):534-539 (1996).
Gold et al. *Annu. Rev. Biochem.*, 64:763-797 (1995).
Goodman *Annu. Rev. Neurosci.*, 19:341-377 (1996).
GrandPré et al. *Nature*, 403:439-444 (2000).
Hong et al. *Cell*, 97(7):927-941 (1999).
Isner et al. *Lancet*, 348:370-374 (1996).
Kasus-Jacobi et al. *Oncogene*, 19(16):2052-2059 (2000).
Keeling et al. *Oncogene*, 15(6):691-700 (1997).
Kohler et al. *Nature*, 256:495-497 (1975).
Kolodkin et al. *Cell*, 75(7):1389-1399 (1993).
Meier et al. *J. Neuropathol. Exp. Neurol.*, 58(10):1099-1110 (1999).
Mey et al. *J. Hirnforschung*, 33:673-702 (1992).
Mimms et al. *Virol.*, 176(2):604-619 (1990).
Ming et al. *Neuron*, 19(6):1225-1235 (1997).
Monnier et al. *Nature*, 419:392-395 (2002).
Mühlhauser *Circ. Res.*, 77:1077-1086 (1995).
Müeller *Curr. Biol.*, 6(11):1497-1502 (1996).
Müeller *Annu. Rev. Neurosci.*, 22:351-388 (1999).
Nielsen et al. *Science*, 254:1497-1500 (1991).
Püschel et al. *Neuron*, 14(5):941-948 (1995).
Raper et al. *Neuron*, 4(1):21-29 (1990).
Routbort et al. *Neurosci.*, 94(3):755-765 (1999).
Santoro et al. *Proc. Natl. Acad. Sci. USA*, 94:4262-4266 (1997).
Schaper et al. *Circ. Res.*, 79:911-919 (1996).
Schnell et al. *Nature*, 343:269-272 (1990).
Serafini et al. *Cell*, 87(6):1001-1014 (1996).
Sharp *Genes Dev.*, 13:139-141 (1999).
Sperry *Proc. Natl. Acad. Sci. USA*, 50:703-710 (1963).
Stahl et al. *Neuron*, 5(5):735-743 (1990).
Steinecke et al. *Meth. Cell Biol.*, "Ribozymes", Chapter 33, Galbraith, eds. Academic Press, Inc. 50:449-460 (1995).
Tessier-Lavigne et al. *Science*, 274:1123-1133 (1996).
Verma et al. *Nature*, 389:239-242 (1997).
Vielmetter et al. *Exp. Brain Res.*, 81(2):283-287 (1990).
Vielmetter et al. *J. Cell Biol.*, 127(6):2009-2020 (1994).
Walter et al. *Development*, 101(4):685-696 (1987).
Walter et al. *Development*, 101:909-913 (1987).
Walter et al. *J. Physiol.*, 84:104-110 (1990).
Wang et al. *Nat. Med.*, 2(6):714-716 (1996).
Wang et al. *J. Neurosci.*, 19(12):4938-4947 (1999).
Yu et al. *Nat. Neurosci.*, 4(Suppl):1169-1176 (2001).

* cited by examiner

TEMPORAL NASAL

1nM RGM-AP, COS-7 CELLS 1nM RGM-AP, NEOGENIN CELLS

A Control

Temporal

Nasal

B +300 nm Neogenin (1-1027)

Temporal

Nasal

Figure 4. *cont.*
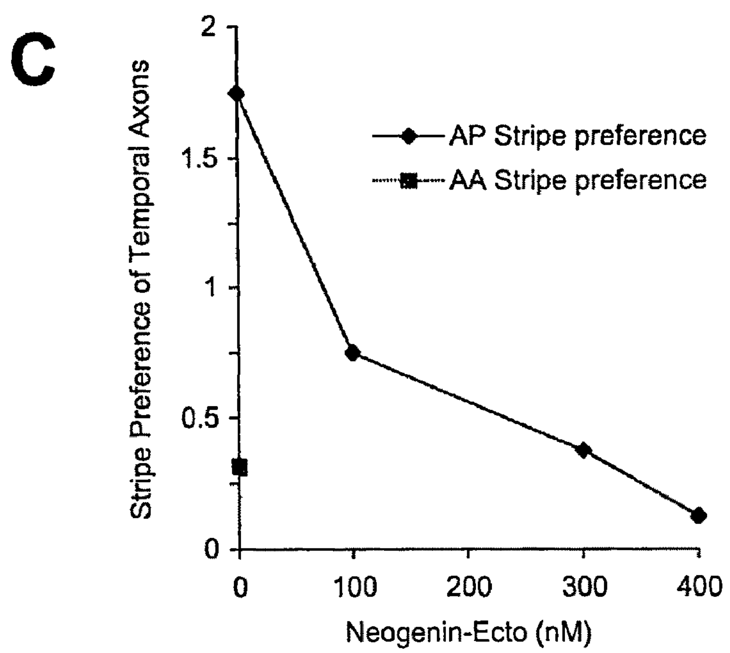
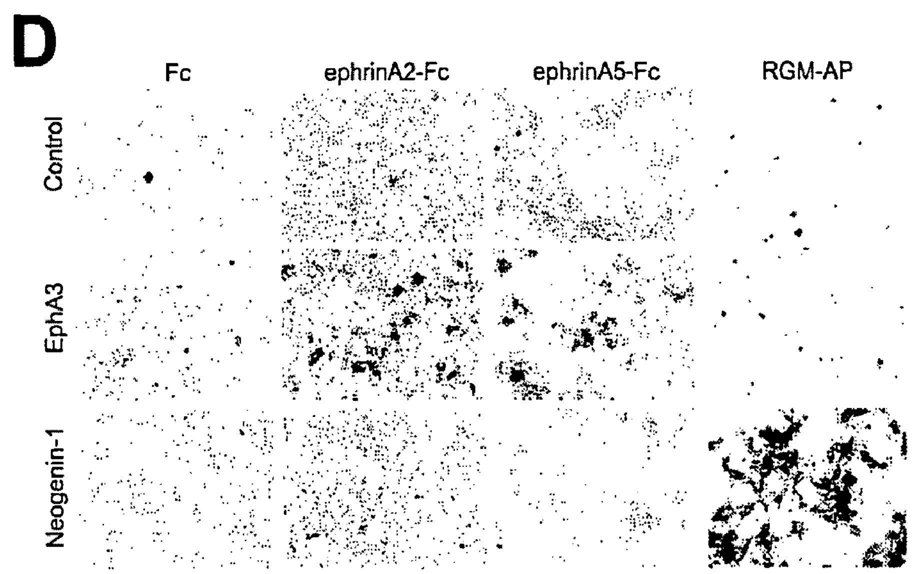

FIGURE 5

```
                    MAAEREAGRLLCTSSSRRCCPPPPLLLLLPLLLLLGRPASGAAA
TKSGSPPQSAGASVRTFTPFYFLVEPVDTLSVRGSSVILNCSAYSEPSPNIEWKKDGT
FLNLESDDRRQLLPDGSLFISNVVHSKHNKPDEGFYQCVATVDNLGTIVSRTAKLTVA
GLPRFTSQPEPSSVYVGNSAILNCEVNADLVPFVRWEQNRQPLLLDDRIVKLPSGTLV
ISNATEGDGGLYRCIVESGGPPKFSDEAELKVLQDREEIVDLVFLMRPSSMMKVTGQR
AVLPCVVSGLPAPVVRWMKNEEVLDTESSGRLVLLAGGGLEISDVTEDDAGTYFCIAD
NGNKTVEAQAELTVQVPPGFLKQPANIYAHESMDIVFECEVTGKPTPTVKWVKNGDVV
IPSDYFKIVKEHNLQVLGLVKSDEGFYQCIAENDVGNAQAGAQLIILEHAPATTGPLP
SAPRDVVASLVSTRFIKLTWRTPASDPHGDNLTYSVFYTKEGVDRERVENTSQPGEMQ
VTIQNLMPATVYIFKVMAQNKHGSGESSAPLRVETQPEVQLPGPAPNIRAYATSPTSI
TVTWETPLSGNGEIQNYKLYYMEKGTDKEQDIDVSSHSYTINGLKKYTEYSFRVVAYN
KHGPGVSTQDVAVRTLSDVPSAAPQNLSLEVRNSKSIVIHWQPPSSTTQNGQITGYKI
RYRKASRKSDVTETLVTGTQLSQLIEGLDRGTEYNFRVAALTVNGTGPATDWLSAETF
ESDLDETRVPEVPSSLHVRPLVTSIVVSWTPPENQNIVVRGYAIGYGIGSPHAQTIKV
DYKQRYYTIENLDPSSHYVITLKAFNNVGEGIPLYESAVTRPHTVPDPTPMMPPVGVQ
ASILSHDTIRITWADNSLPKHQKITDSRYYTVRWKTNIPANTKYKNANATTLSYLVTG
LKPNTLYEFSVMVTKGRRSSTWSMTAHGATFELVPTSPPKDVTVVSKEGKPRTIIVNW
QPPSEANGKITGYIIYYSTDVNAEIHDWVIEPVVGNRLTHQIQELTLDTPYYFKIQAR
NSKGMGPMSEAVQFRTPKALGSAGKGSRLPDLGSDYKPPMSGSNSPHGSPTSPLDSNM
LLVIIVSVGVITIVVVVVIAVFCTRRTTSHQKKKRAACKSVNGSHKYKGNCKDVKPPD
LWIHHERLELKPIDKSPDPNPVMTDTPIPRNSQDITPVDNSMDSNIHQRRNSYRGHES
EDSMSTLAGRRGMRPKMMMPFDSQPPQPVISAHPIHSLDNPHHHFHSSSLASPARSHL
YHPSSPWPIGTSMSLSDRANSTESVRNTPSTDTMPASSSQTCCTDHQDPEGATSSSYL
ASSQEEDSGQSLPTAHVRPSHPLKSFAVPAIPPPGPPLYDPALPSTPLLSQQALNHHI
HSVKTASIGTLGRSRPPMPVVVPSAPEVQETTRMLEDSESSYEPDELTKEMAHLEGLM
KDLNAITTA."
```

FIGURE 6A

```
   1 GGGGGCCGCG CGGGCCGGGC CGGGCCGGGC TGGAGCCGAG CCCTGCGGCG CAGAGACCGG
  61 CTGAGGCGCG CTGAGGGAAG GGCGCGAGCG CTCCGCGGCG CTATCGCCGC CGCCGCCGCC
 121 GCCACTCGTG GGGTAGAGAT GGCGGCGGAG CGCGAAGCCG GGCGACTCCT CTGCACCTCC
 181 TCCTCCCGGC GCTGCTGTCC GCCACCGCCG CTGCTGCTGT TGCTGCCGCT GCTGCTGCTG
 241 CTCGGACGCC CGGCGTCCGG CGCCGCGGCC ACGAAGAGCG GCTCCCCGCC GCAGTCCGCA
 301 GGAGCCAGTG TTCGAACATT CACTCCGTTT TATTTTCTGG TGGAGCCAGT AGACACCCTC
 361 TCAGTTAGAG GCTCTTCTGT TATATTAAAT TGCTCGGCAT ATTCTGAGCC CTCTCCAAAC
 421 ATTGAATGGA AGAAAGATGG GACTTTTTTA AACTTAGAAT CAGATGATCG ACGCCAGCTA
 481 CTCCCAGATG GATCTTTATT CATCAGCAAC GTGGTGCATT CCAAACACAA TAAGCCTGAC
 541 GAAGGTTTCT ATCAGTGTGT AGCCACTGTG GATAATCTTG GAACCATTGT CAGCAGAACA
 601 GCCAAGCTCA CAGTAGCAGG TCTTCCAAGA TTTACCAGCC AACCAGAACC TTCTTCAGTC
 661 TATGTTGGAA ACAGTGCAAT TCTGAATTGT GAAGTTAATG CAGATTTGGT CCCATTTGTT
 721 AGGTGGGAAC AGAATCGACA GCCCCTTCTT CTAGATGACA GGATTGTCAA ACTTCCAAGT
 781 GGAACACTGG TTATCAGCAA TGCTACTGAA GGAGATGGGG GACTCTACCG CTGCATTGTT
 841 GAAAGTGGTG GGCCACCAAA GTTTAGTGAC GAAGCTGAAT TGAAAGTTCT TCAAGATCGT
 901 GAGGAAATTG TAGACTTGGT ATTTCTGATG CGACCATCTT CTATGATGAA AGTCACTGGT
 961 CAGCGTGCAG TGTTGCCATG TGTTGTCTCA GGGCTTCCTG CTCCAGTCGT TAGATGGATG
1021 AAAAACGAAG AAGTGCTTGA CACAGAAAGC TCTGGCAGGT TGGTCTTGCT AGCAGGAGGT
1081 GGCTTGGAGA TCAGTGATGT CACTGAGGAT GATGCTGGGA CTTATTTTTG CATAGCTGAT
1141 AATGGAAATA AGACAGTTGA AGCTCAGGCG GAGCTTACTG TGCAAGTGCC ACCTGGATTC
1201 TTGAAACAAC CTGCTAACAT ATATGCTCAC GAATCCATGG ACATTGTATT TGAATGTGAA
1261 GTCACTGGGA AGCCAACTCC AACTGTGAAG TGGGTCAAGA ATGGGGATGT GGTTATCCCC
1321 AGTGATTACT TTAAAATTGT AAAGGAACAT AATCTTCAAG TTTTGGGTCT GGTGAAATCA
1381 GATGAAGGGT TCTATCAATG CATTGCTGAG AATGATGTTG GAAATGCACA AGCTGGAGCC
1441 CAGCTGATAA TCCTTGAGCA TGCACCAGCC ACAACGGGAC CACTACCTTC AGCTCCTCGA
1501 GACGTCGTGG CCTCCCTGGT CTCTACTCGC TTCATTAAAT TGACATGGCG TACACCTGCA
1561 TCAGACCCTC ATGGAGACAA TCTCACCTAC TCTGTGTTCT ACACCAAGGA AGGGGTTGAT
1621 AGGGAGCGTG TTGAGAATAC CAGCCAGCCA GGAGAGATGC AGGTGACTAT TCAAAACTTG
1681 ATGCCAGCAA CTGTGTACAT CTTCAAAGTT ATGGCTCAAA ATAAGCATGG CTCTGGAGAA
1741 AGTTCAGCTC CTCTTCGAGT AGAGACACAG CCTGAGGTTC AGCTCCCTGG CCCAGCACCT
1801 AATATCCGTG CTTATGCAAC GTCACCTACT TCTATCACTG TCACCTGGGA AACACCGTTA
1861 TCTGGCAATG GGGAAATTCA AAATTACAAA TTGTACTACA TGGAAAAAGG AACTGATAAA
1921 GAACAGGATA TTGATGTTTC AAGTCACTCC TACACCATTA ATGGACTGAA GAAATACACA
1981 GAATATAGTT TCCGAGTGGT GGCCTACAAT AAACATGGTC CTGGAGTTTC TACACAAGAT
2041 GTTGCTGTTC GAACATTATC AGATGTTCCC AGTGCTGCTC CTCAGAATCT GTCCTTAGAA
2101 GTGAGAAATT CAAAGAGTAT AGTGATCCAC TGGCAGCCCC CTTCCTCAAC CACACAAAAT
2161 GGGCAGATAA CTGGCTACAA GATTCGATAT CGAAAGGCCT CCCGAAAAAG TGATGTCACT
2221 GAGACCTTGG TAACTGGGAC ACAGCTGTCT CAGCTGATTG AAGGTCTTGA TCGGGGGACA
2281 GAATATAACT TCCGAGTCGC TGCTCTCACA GTCAATGGTA CAGGTCCAGC AACTGATTGG
2341 CTGTCTGCTG AAACTTTTGA AAGCGACCTA GATGAAACTC GTGTTCCTGA AGTGCCCAGC
2401 TCTCTTCATG TCCGTCCGCT CGTCACTAGC ATTGTAGTGA GCTGGACTCC TCCAGAGAAC
2461 CAGAACATTG TGGTCCGAGG TTATGCCATC GGTTACGGCA TTGGCAGCCC TCATGCCCAG
2521 ACCATCAAAG TGGACTATAA ACAACGTTAT TACACCATTG AAAACTTGGA TCCAAGCTCT
2581 CATTACGTGA TTACCTTGAA AGCATTTAAC AATGTTGGCG AAGGCATCCC CCTTTATGAG
2641 AGTGCTGTGA CCAGACCTCA CACAGTGCCA GATCCCACTC CCATGATGCC ACCAGTGGGA
2701 GTTCAGGCTT CCATTCTGAG TCACGACACC ATAAGGATTA CCTGGGCAGA CAACTCCCTG
2761 CCCAAACACC AGAAGATTAC AGACTCCCGC TACTACACAG TCCGGTGGAA GACCAACATC
2821 CCAGCAAACA CGAAGTACAA GAATGCAAAT GCAACGACGT TAAGCTATTT GGTTACTGGT
2881 TTAAAGCCAA ATACGCTCTA TGAGTTCTCT GTGATGGTGA CCAAAGGCAG AAGGTCAAGC
2941 ACGTGGAGTA TGACAGCTCA TGGCGCTACC TTTGAATTAG TTCCTACTTC TCCACCTAAG
3001 GATGTGACAG TTGTGAGTAA GGAAGGAAAA CCTAGAACCA TCATAGTGAA CTGGCAGCCT
3061 CCCTCTGAAG CTAACGGCAA GATTACAGGT TACATCATCT ATTACAGCAC GGATGTGAAT
3121 GCAGAGATAC ATGACTGGGT TATTGAACCA GTTGTGGGAA ACAGACTGAC TCACCAGATT
3181 CAAGAGTTAA CACTTGATAC GCCATACTAC TTCAAAATCC AGGCCCGGAA CTCAAAGGGC
3241 ATGGGGCCCA TGTCTGAAGC TGTACAGTTC AGAACACCTA AAGCCTTAGG GTCAGCAGGA
3301 AAAGGAAGCC GACTACCAGA CCTGGGATCT GACTACAAAC CTCCAATGAG TGGCAGCAAC
3361 AGCCCTCACG GGAGCCCCAC CTCCCCTCTG GACAGCAACA TGCTGCTGGT CATCATTGTC
3421 TCTGTTGGCG TCATCACTAT CGTGGTGGTT GTGGTCATTG CTGTCTTTTG TACCCGGCGC
```

FIGURE 6B

```
3481 ACCACCTCTC ACCAGAAAAA GAAACGAGCT GCGTGCAAAT CAGTGAATGG CTCCCATAAG
3541 TACAAGGGCA ATTGCAAAGA TGTGAAGCCT CCAGACCTAT GGATCCATCA CGAGAGACTA
3601 GAGTTGAAGC CTATTGACAA GTCTCCAGAT CCTAACCCTG TCATGACTGA TACTCCAATC
3661 CCTCGAAACT CTCAAGATAT CACACCAGTG GACAATTCCA TGGATAGCAA TATCCATCAA
3721 AGGCGGAATT CATACAGAGG GCATGAGTCA GAGGACAGCA TGTCTACACT GGCTGGAAGG
3781 AGGGGAATGA GACCAAAAAT GATGATGCCC TTTGACTCTC AGCCACCTCA GCCTGTGATT
3841 AGTGCCCATC CCATCCATTC CCTCGATAAC CCTCACCATC ATTTCCACTC CAGCAGCCTC
3901 GCTTCTCCAG CCCGCAGTCA TCTCTACCAC CCAAGCAGCC CATGGCCCAT TGGCACATCC
3961 ATGTCCCTTT CAGACAGGGC CAATTCCACA GAATCTGTTC GAAATACCCC CAGCACGGAC
4021 ACCATGCCAG CGTCCTCGTC TCAGACGTGC TGCACTGACC ATCAGGACCC TGAGGGTGCT
4081 ACTAGCTCCT CTTACTTGGC CAGCTCCCAA GAGGAAGACT CAGGCCAGAG TCTTCCCACA
4141 GCCCATGTCC GCCCTTCCCA CCCTCTGAAG AGCTTCGCTG TGCCAGCAAT CCCACCCCCA
4201 GGACCTCCTC TCTATGATCC TGCACTGCCA AGCACACCAT TACTGTCCCA GCAAGCTCTG
4261 AACCATCACA TTCACTCAGT GAAAACAGCC TCCATCGGGA CGTTAGGAAG GAGCCGGCCT
4321 CCTATGCCAG TGGTTGTTCC GAGTGCCCCT GAAGTACAGG AGACCACCAG GATGCTGGAA
4381 GACTCCGAGA GTAGCTATGA ACCAGATGAG CTGACCAAAG AGATGGCCCA CCTGGAAGGA
4441 CTAATGAAGG ACCTAAATGC CATCACAACA GCCTGATGAC CTTCGCCTGG ACATGACTCC
4501 AAGCCTGAGT CTACAAGTCT CGGAACTTAA CCTTGAAAAC AAGGAATTGT ACAGAGTACG
4561 AGAGGACAGC ACTTGAGAGC AGGAGCCAGC AAACCAGCCA GTGCCTCCAT GTGGGGTTGG
4621 CTCCAGGCAC AGCCACCTGC CTTCTCCTGG TCAGCCTGGA TTACACTTGT GTGGAGGCAG
4681 CTTCCCTTTG CCTGCTGAGA GCCTGCAGGA CTGGGCACTA TGGGCCAAAA TTTTGTGTCC
4741 AGGGAAGAGG CAAGAAGTAC GACCTGCCTT TTGCTTTGTG GTCAGTGGCT TGTGTCTTTG
4801 TGCTGCAACT GCATCACTTT TATGGAGTGT AGACATTGGC ATTTATGTAC AATTTTGTGT
4861 CCTATTTTAT TTTACCTTAA AACACTATCA GAAGCCAAGG GAGTCTGTGA TGTTCTCTCA
4921 AGCAGTTGAC ACTTGACTGT GGTTCCAGTT ACTTACGGAA AGTCATCAAC AGTGAGGTTG
4981 TTTGACACCA CTGACAGGCA TTGGCTTGTT GTGGGTTTCA TTTTTATTCT TAATTCTGAG
5041 ACATTGCATC CTCTGCCAGC TGTTAATCCA TCACTTTGAG GGGAGGACAT GTTGCATTGC
5101 TGTTTGTAAG CTTTTTTATT ATTTTTTTAT TATAATTATT AAAGGCCTGA CTTTCTCCTC
5161 TCAAAAAAAA AAAAAAAAAA AAAAAAAAAA AAAAAAAA
```

MODULATORS AND MODULATION OF THE INTERACTION BETWEEN RGM AND NEOGENIN

CROSS REFERENCE TO RELATED APPLICATIONS

This application is a continuation application under 35 USC §371 to PCT/US03/20147, filed Jun. 26, 2003, which claims the benefit of U.S. application Ser. No. 60/392,062, filed Jun. 26, 2002.

TECHNICAL FIELD OF THE INVENTION

This invention is related to the field of neuroscience and neurology. In particular embodiments it is related to the area of axon guidance cues and their modulators, and neurological drug screening using repulsive guidance molecules and Neogenin.

BACKGROUND OF THE INVENTION

One of the most important mechanisms in formation of embryonic nervous systems is the guidance of axons and growth cones by directional guidance cues (Goodman, Annu. Rev. Neurosci. 19 (1996), 341-77; Mueller, Annu. Rev. Neurosci 22, (1999), 351-88). A suitable model system for studying this guidance process is the retinotectal system of vertebrates. In the chick embryo approximately 2 million retinal ganglion cell (RGC) axons leave each eye and grow towards the contralateral tectum opticum to form a precise map (Mey & Thanos, (1992); J. Hirnforschung 33,673-702). Having arrived at the anterior pole of the optic tectum, RGC axons start to invade their tectal target to find their target neurons. Mapping occurs in such a way that RGC axons from nasal retina project to posterior tectum and temporal axons to anterior tectum. Along the dorso-ventral axis, axons coming from dorsal retina terminate in ventral tectum, whereas those from ventral retina end up in dorsal tectum. Ultimately, a precise topographic map is formed, where neighborhood relationships in the retina are preserved in the tectum so that axons from neighboring ganglion cells in the retina synapse with neighboring tectal neurons. Most important for formation of this map are graded tectal guidance cues, read by retinal growth cones carrying corresponding receptors which also show a graded distribution (Sperry, Proc. Natl. Acad. Sci. USA 50 (1963), 703710; Bonhoeffer & Gierer, Trends Neurosci. 7 (1984) 378-381).

Position of each retinal growth cone in the tectal field is therefore determined by two sets of gradients: receptor gradients on in-growing retinal axons and growth cones and ligand gradients on tectal cells (Gierer, Development 101 (1987), 479-489). The existence of the graded tectal ligands has been postulated from anatomical work. Their identification, however, proved to be extremely difficult and was only made possible with the development of simple in vitro systems (Walter ; Development 101 (1987), 685-96; Cox, Neuron 4 (1990), 31-7). In the stripe assay, RGC axons grow on a membrane carpet, consisting of alternating lanes of anterior (a) and posterior (p) tectal membranes. On these carpets, temporal retinal axons grow on anterior tectal membranes and are repelled by the posterior lanes, whereas nasal axons do not distinguish between a and p membranes (Walter, Development 101 (1987), 685-96). The same specificity is also observed in the growth cone collapse assay (Raper & Kapfhammer, Neuron 4 (1990), 21-29) where temporal retinal growth cones collapse after addition of posterior tectal membrane vesicles but do not react to anterior tectal vesicles and where nasal growth cones are insensitive to either type of vesicles (Cox, (1990), loc. cit.). In both assay systems, treatment of posterior tectal membranes with the enzyme phosphatidylinositol-specific phospholipase C (PI-PLC) (which cleaves the lipid anchor of glycosylphosphatidylinositol (GPI)-linked proteins) removed their repellent and collapse-inducing activity (Walter, J. Physiol 84 (1990), 104-10).

One of the first repulsive guidance molecules identified in the retinotectal system of chick embryos was a GPI-anchored glycoprotein with a molecular weight of 33/35 kDa (Stahl, Neuron 5 (1990), 735-43). This 33/35 kDa molecule, later termed RGM (Repulsive Guidance Molecule), was active in both stripe and collapse-assays and was shown to be expressed in a low-anterior high-posterior gradient in the embryonic tecta of chick and rat (Mueller, Curr. Biol. 6 (1996), 1497-502; Mueller, Japan Scientific Societies Press (1997), 215-229). Due to the abnormal biochemical behavior of RGM, the precise amino acid sequence was not easily obtainable. RGM was described as a molecule which is active during vertebrate development. Interestingly, RGM is down-regulated in the embryonic chick tectum after E12 and in the embryonic rat tectum after P2 and completely disappears after the embryonic stages (Muller (1992), Ph. D thesis University of Tübbingen; Müller (1997) Japan Scientific Societies, 215-229). In 1996, Müller (loc. cit.) showed that CALI (chromophore-assisted laser inactivation) of RGM eliminates the repulsive guidance activity of posterior tectal membranes. However, due to the presence of other guidance molecules, in particular of RAGS (repulsive axon guidance signal) and ELF-1 (Eph ligand family 1), a complete elimination of guidance was not always detected and it was speculated that RGM acts in concert with RAGS (now termed ephrin-A5) and ELF-1 (ephrin-A2). It was furthermore envisaged that RGM may be a co-factor potentiating the activity of RAGS and ELF-1 in embryonic guidance events.

In 1980/81 the group of Aguayo found that, when peripheral neurons are transplanted/grafted into injured CNS of adult, axon growth of CNS neurons is induced (David, Science 214 (1981), 931-933). Therefore, it was speculated that CNS neurons have still the ability and capacity of neurite-outgrowth and/or regeneration, if a suitable environment would be provided. Furthermore, it was speculated that "CNS-neuron regeneration inhibitors" may exist.

In 1988, Caroni and Schwab (Neuron 1,85-96) described two inhibitors of 35 kDa and 250 kDa, isolated from rat CNS myelin (NI-35 and NI-250; see also Schnell, Nature 343 (1990) 269-272; Caroni, J. Cell Biol. 106 (1988), 1291-1288).

In 2000, the DNA encoding for NI-220/250 was deduced and the corresponding potent inhibitor of neurite growth was termed Nogo-A (Chen, Nature 403 (2000), 434-438). The membrane-bound Nogo turned out to be a member of the reticulon family (GrandPre, Nature 403 (2000), 439-444).

Further factors which mediate neuronal outgrowth inhibition have first been isolated in grasshoppers, and termed "fasciclin IV" and later "collapsin" in chicken. These inhibitors belong to the so-called semaphorin family. Semaphorins have been reported in a wide range of species and described as transmembrane proteins (see, inter alia, Kolodkin Cell 75 (1993) 1389-99, Püschel, Neuron 14 (1995), 941-948). Yet, it was also shown that not all semaphorins have inhibitory activity. Some members of the family, e.g. semaphorin E, act as an attractive guidance signal for cortical axons (Bagnard, Development 125 (1998), 5043-5053).

A further system of repulsive guidance molecules is the ephrin-Eph system. Ephrins are ligands of the Eph receptor kinases and are implicated as positional labels that may guide the development of neural topographic maps Flanagan, Ann. Rev. Neurosc. 21 (1998), 309-345). Ephrins are grouped in two classes, the A-ephrins which are linked to the membrane by a glycosylphosphatidylinositol-anchor (GPIanchor) and the B-ephrins carrying a transmembrane domain (Eph nomenclature committee 1997). Two members of the A-ephrins, ephrin-A2 and ephrin-A5, expressed in low anterior-high posterior gradients in the optic tectum, have recently been shown to be involved in repulsive guidance of retinal ganglion cell axons in vitro and in vivo (see, inter alia (Drescher, Cell 82 (1995), 359-70; Cheng, Cell 79 (1994), 157-168; Feldheim, Neuron 21 (1998), 563-74; Feldheim, Neuron 25 (2000), 563-74). Considering the fact that a plurality of physiological disorders or injuries are related to altered cellular migration processes, the technical problems underlying the present invention was to provide for means and methods for modifying developmental or cellular (migration) processes which lead to disease conditions.

The Ephrin, Semaphorin, Slit, and RGM families of extracellular guidance cues specify axonal trajectories during nervous system development[1-3]. The netrins are a family of proteins that are profound modulators of growth of developing axons, functioning as attractants for some axons and repellents of other axons. As such, the modulation of these effects provides an important therapeutic pathway for assisting the regeneration of axons in adult nervous system (e.g. following injury or trauma). While neuronal receptors have been identified for most axonal guidance cues, the mechanism by which the recently sequenced RGM protein (WO 02/051438) acts has not been clarified[3]. As described in part above, chick RGM is expressed in a posterior to anterior tectal gradient and has been shown to collapse temporal but not nasal retinal growth cones[3]. After signal peptide cleavage and GPI addition, the cell surface RGM is proteolytically processed to a mature active form of 33 kDa[3].

The ability to construct high-throughput and specific pharmaceutical screens for modulators of guidance cues (such as RGM) has been limited by the lack of identifiable receptors. Identifying receptors on axons that mediate neural responsiveness to guidance cues will provide key targets for identifying lead pharmaceuticals for therapeutic intervention in the nervous system (see, for example, U.S. Pat. Nos. 6,087,326 and 5,747,262). Accordingly, because RGM has a demonstrated role in axon growth, it would be desirable to accurately identify the receptor through which RGM acts such that targeted screens could be conducted.

Neogenin is known to share sequence similarity with the Netrin receptor Deleted in Colorectal Cancer (DCC). The sequence for the Neogenin gene has been described (for example, Keeling S L, Gad J M, Cooper H M. "Mouse Neogenin, a DCC-like molecule, has four splice variants and is expressed widely in the adult mouse and during embryogenesis." Oncogene. Aug. 7, 1997;15(6):691-700. GenBank NT_039474; NM_008684) and it has been previously theorized that it is an interaction with Netrin-1 that is responsible for signaling through Neogenin. However, as described in detail herein, the present inventors have determined the true physiological ligand for Neogenin.

SUMMARY OF THE INVENTION

The invention identifies Neogenin as the receptor for Repulsive Guidance Molecule. Accordingly, the invention envisions the use of the previously described Neogenin and RGM molecules in combinations and methods which could not previously have been suggested. In particular, the invention allows for targeted screening assays and the development of inhibitors capable of specifically inhibiting the interaction between RGM and Neogenin.

The invention provides efficient methods of identifying agents, compounds or lead compounds for agents capable of modulating Neogenin cellular function. Generally, these screening methods involve assaying for compounds which modulate mammalian Neogenin interaction with a natural mammalian RGM. A wide variety of assays for binding agents are provided including labeled in vitro protein-protein binding assays, immunoassays, cell based assays, animal based assay, etc. Preferred methods are amenable to automated, cost-effective high throughput screening of chemical libraries for lead compounds. Such libraries encompass candidate agents of numerous chemical classes, though typically they are organic compounds; preferably small organic compounds and are obtained from a wide variety of sources including libraries of synthetic or natural compounds. Identified agents find use in the pharmaceutical industries for animal and human trials; for example, the agents may be derivatized and rescreened in in vitro and in vivo assays to optimize activity and minimize toxicity for pharmaceutical development.

In vitro binding assays employ a mixture of components including mammalian Neogenin protein, which may be part of a fusion product with another peptide or polypeptide, e.g. a tag for detection or anchoring, etc. The assay mixtures comprise a natural extracellular mammalian Neogenin binding target, such as a RGM. While native binding targets may be used, it is frequently preferred to use portions (e.g. peptides) thereof so long as the portion provides binding affinity and avidity to the subject mammalian Neogenin protein conveniently measurable in the assay. The assay mixture also comprises a candidate pharmacological agent and typically, a variety of other reagents such as salts, buffers, neutral proteins, e.g. albumin, detergents, protease inhibitors, nuclease inhibitors, antimicrobial agents, etc. The mixture components can be added in any order that provides for the requisite bindings and incubations may be performed at any temperature which facilitates optimal binding. The mixture is then incubated under conditions whereby, but for the presence of the candidate pharmacological agent, the mammalian Neogenin protein specifically binds the cellular binding target, portion or analog with a reference binding affinity. Incubation periods are likewise selected for optimal binding but also minimized to facilitate rapid, high-throughput screening.

After incubation, the agent-biased binding between the mammalian Neogenin protein and one or more binding targets is detected. A separation step is often initially used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). One of the components usually comprises or is coupled to a label. The label may provide for direct detection such as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the mammalian Neogenin protein to the target in the absence of the agent as compared with the binding affinity in the presence of the agent indicates that the agent modulates the binding of the mammalian Neogenin protein to the mammalian RGM. Analogously, in a cell-based transcription assay, a difference in the mammalian Neogenin transcriptional induction in the presence and absence of an agent indicates the agent modulates vertebrate such induced transcription. A difference, as used herein, is statistically significant and preferably represents at least a 50%, more preferably at least a 90% difference.

The invention provides methods and compositions for identifying pharmacological agents useful in the diagnosis or treatment of neurological disease or injury. In particular, the invention provides mixtures comprising an isolated (RGM) and an isolated Neogenin receptor capable of specifically binding said RGM. The general methods involve incubating a mixture comprising an isolated RGM, an isolated Neogenin receptor, and a candidate pharmacological agent, and determining if the presence of the agent modulates the binding of the RGM to the receptor. Specific agents provide lead compounds for pharmacological agents useful in the diagnosis or treatment of neurological disease or injury.

It is an object of the present invention to provide a method of monitoring the interaction of a RGM and a Neogenin.

Another object of the invention is to provide a method for monitoring the interaction between RGM and Neogenin so that agonists and antagonists can be identified.

Another object of the invention is to provide a polypeptide useful for antagonizing the interaction between a RGM and a Neogenin receptor.

Another object of the invention is to provide a polypeptide useful for antagonizing the interaction between RGM and Neogenin.

These and other objects of the invention are achieved by one or more of the embodiments described below. In one embodiment a method of monitoring the interaction of a RGM and a Neogenin receptor is provided. The method comprises the steps of:

- contacting a first protein comprising an RGM with a second protein which comprises Neogenin under conditions where a domain of the RGM binds to a domain of the Neogenin;
- determining the binding of the first protein to the second protein or second protein to the first protein.

According to another aspect of the invention a method is provided for monitoring the interaction between a RGM and a Neogenin. The method comprises the steps of:

- contacting a fusion protein comprising an RGM domain with cells which express a Neogenin;
- detecting the fusion protein comprising the RGM domain which binds to the cells.

As another aspect of the invention a method is provided for monitoring the interaction between a RGM and Neogenin. The method comprises the steps of:

- contacting a protein comprising a RGM domain with cells which express a polypeptide comprising Neogenin;
- detecting the protein comprising the RGM domain which binds to the cells.

As still another aspect of the invention a polypeptide portion of Neogenin useful for antagonizing the interaction between RGM and Neogenin is provided.

According to still another aspect of the invention a method of monitoring the interaction between a RGM and Neogenin is provided. The method comprises the steps of:

- co-culturing in a matrix (a) embryonic nerve cells with (b) cells which have been transfected with an expression construct encoding a RGM and which express the Neogenin;
- adding to the cells an inhibitor of binding of the RGM and Neogenin;
- determining the axon outgrowth adjacent to the cells which express the RGM in the presence and absence of inhibitor.

As another aspect of the invention a method is provided for monitoring the interaction between a RGM and Neogenin. The method comprises the steps of:

- culturing embryonic nerve cells under conditions in which they display growth cones;
- contacting the embryonic nerve cells with a RGM and an anti-Neogenin antibody;
- observing the effect of the antibody on the collapse of the growth cones.

Yet another aspect of the invention is provided by an antibody preparation which specifically binds to a Neogenin protein.

Yet another aspect of the invention is provided by an antibody specifically targeted to domain(s) involved in the interaction between Neogenin and RGM. In a particular embodiment, such antibodies would be directed towards the FNIII domain(s) of Neogenin.

Yet another aspect of the invention is provided by an antibody preparation which specifically binds to a RGM protein.

RGM is processed proteolytically, and the active domain extends carboxyl from the cut site to the GPI anchorage site. This same region appear to mediate Neogenin binding. Accordingly, antibodies directed to domains within this region would be one aspect of the invention.

Yet another aspect of the invention is provided by a nucleic acid capable of inhibiting the expression of an RGM protein or a Neogenin protein.

The medical applications of such compounds, their agonists, and their antagonists are enormous and include preventing, alleviating or treating various disorders of the nervous system, angiogenic disorders or disorders of the cardio-vascular system and malignancies of different etiology.

(A) Purified recombinant RGM-AP is avoided by temporal axons in a stripe assay.

(B) The binding of a chick RGM-AP to COS-7 cells expressing mouse Neogenin is illustrated. The bound protein is detected as a dark reaction product on the right.

(C) Saturation of RGM-AP to COS-7 expressing Neogenin. Bound RGM-AP activity was determined for each of the indicated concentrations of RGM-AP. The data are the average ±sem of 6 independent determinations.

(D) Scatchard analysis of RGM-AP binding to Neogenin expressing cells. Data from (C) are replotted. The Kd is 230 pM.

(E', E" and E"') Chick-RGM-A-AP, Mouse RGM-A-AP and RGM-B-AP also bind to Neogenin.

Figure 2:
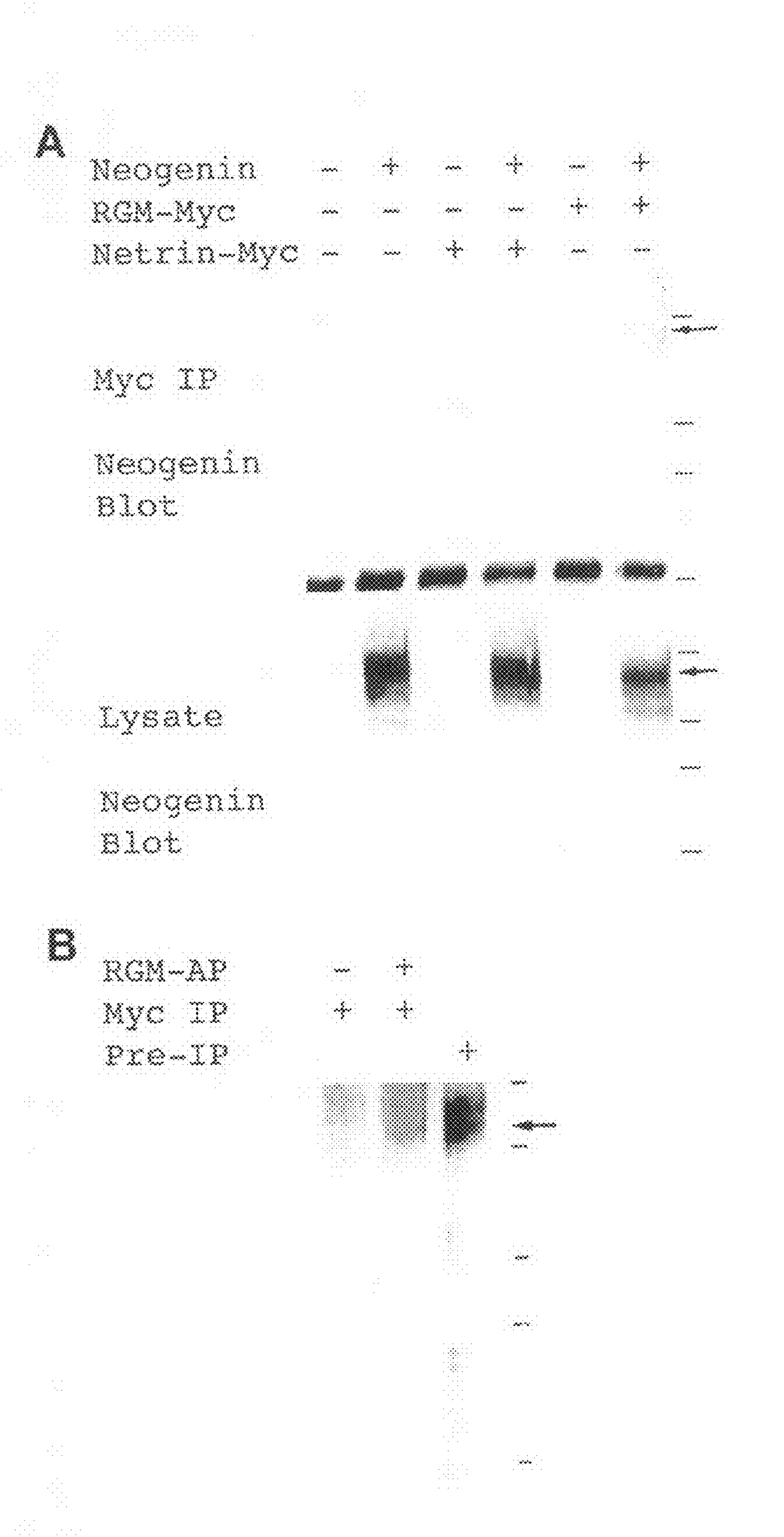

FIG. 2. Physical complex containing RGM and Neogenin.

(A) Co-immunoprecipitation of RGM and Neogenin. HEK293T cells were transfected with plasmids encoding the indicated proteins and immunoprecipitated with anti-Myc antibody resin. The presence of Neogenin protein in the lysates and the immunoprecipitate is illustrated.

(B) RGM affinity chromatography of adult mouse brain. Adult mouse brain membrane fractions were extracted with 2% TritonX-100 and solubilized protein was incubated with or without chick RGM-AP-Myc-His. Protein retained by an anti-Myc antibody resin was analyzed by anti-Neogenin immunoblot.

Figure 3:
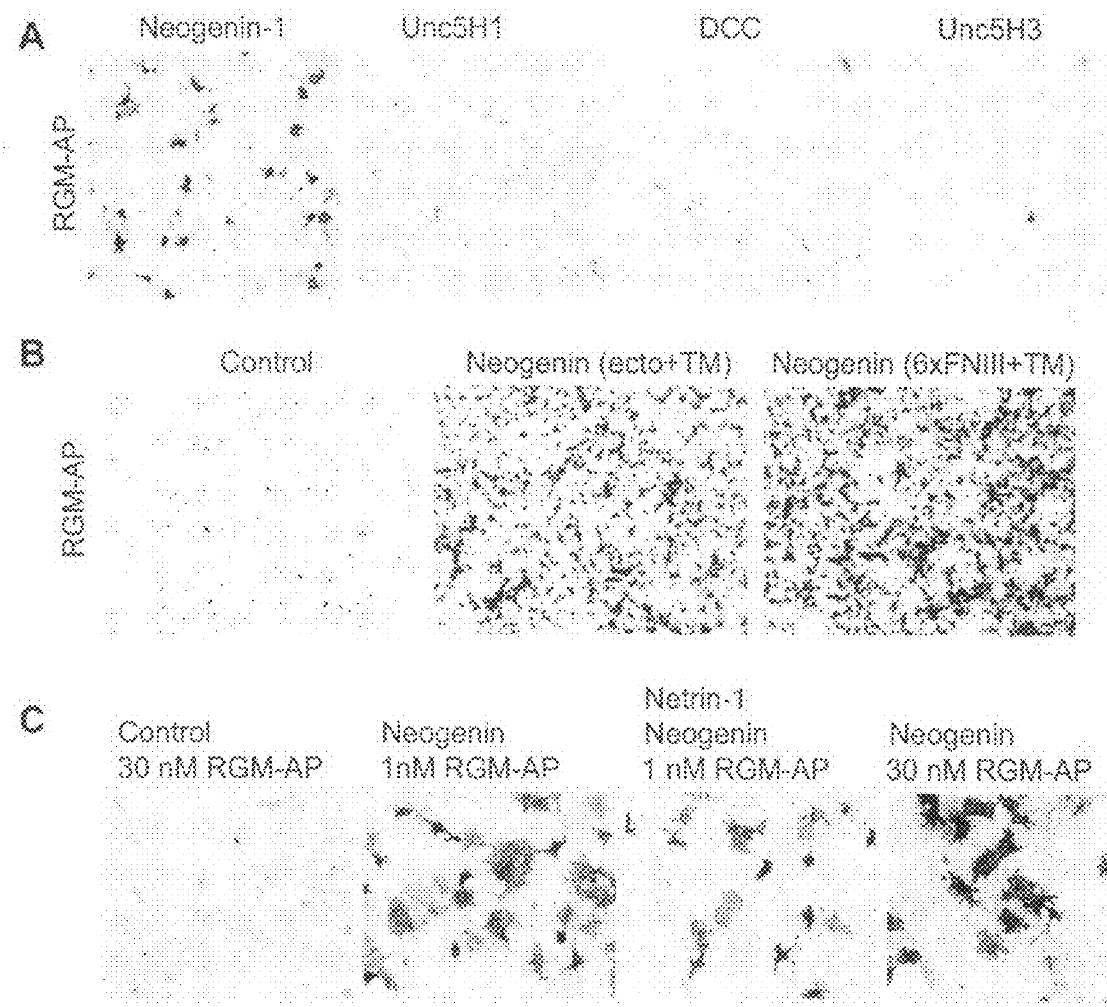

FIG. 3. Specificity of Neogenin interaction with RGM.

(A) RGM-AP binding to COS-7 cells transfected with expression plasmids encoding various Netrin-1 binding proteins.

(B) RGM-AP binds to the FNIII repeats of Neogenin. RGM-AP binding to COS-7 expressing the indicated fragments of Neogenin is illustrated.

(C) Netrin-1 does not alter the binding of RGM-AP to Neogenin. The ability of chick RGM-AP to bind to COS-7 cells expressing wild type mouse Neogenin was assessed in the presence or absence of conditioned medium containing Netrin-1-Myc (100 nM).

Figure 4:
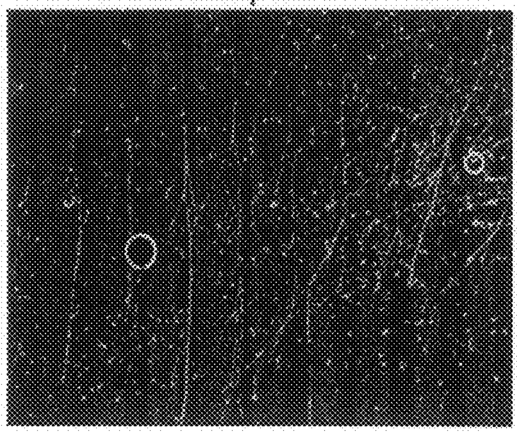
Figure 4:
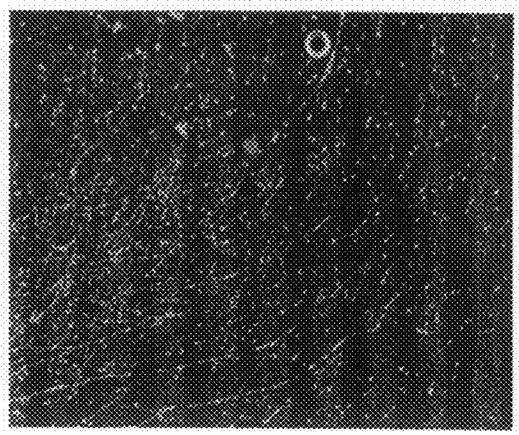
Figure 4:
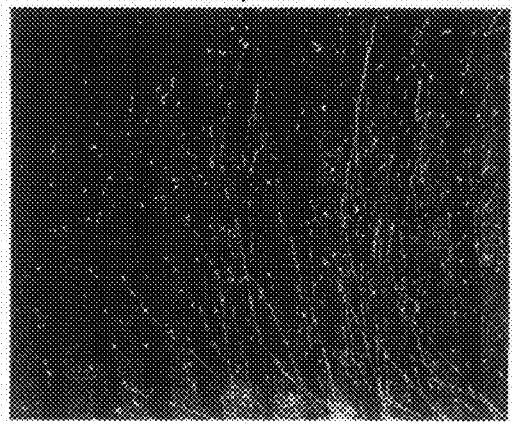
Figure 4:
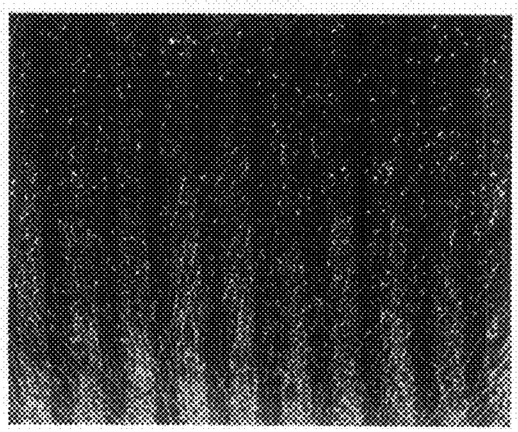

FIG. 4. Dominant negative Neogenin-1 blocks retinotectal axonal preferences.

(A) Retinal ganglion cell axon preference for anterior tectal membranes. Outgrowth from explants from the temporal or nasal chick retina (green) is illustrated on stripes consisting of anterior (black) or posterior (red) tectal membranes.

(B) Retinotectal stripe assay in the presence of soluble ectodomain of Neogenin-1. A preference of temporal axons for anterior membranes observed in (A) is greatly reduced.

(C) Stripe preference as a function of soluble Neogenin ectodomain concentration. Data from 4-16 experiments such as in (A) and (B) were scored for the extend of preference of temporal retinal axons for Anterior versus Posterior stripes (AP) or Anterior versus Anterior stripes (AA). A rating of 2 reflects a complete segregation of axons to the anterior stripes, a rating of 1 reflects still a preference for anterior stripes without complete segregation and 0 is no preference[10,11].

(D) Binding specificity of the RGM/Neogenin and ephrinA/EphA pairs. COS-7 cells were transfected with expression plasmids for Neogenin-1 or EphA3 and then incubated with medium containing Ephrin-A2-Fc, Ephrin-A5-Fc or RGM-AP. Note the specificity of binding. Bound Fc has detected with HRP-conjugated anti-human IgG.

FIG. 5. Amino acid sequence of Neogenin (SEQ ID NO: 1).

FIG. 6. Nucleotide sequence of Neogenin (SEQ ID NO: 2).

(A) Nucleotides 1-3480.

(B) Nucleotides 3481-5199.

DETAILED DESCRIPTION

Figure 1A:
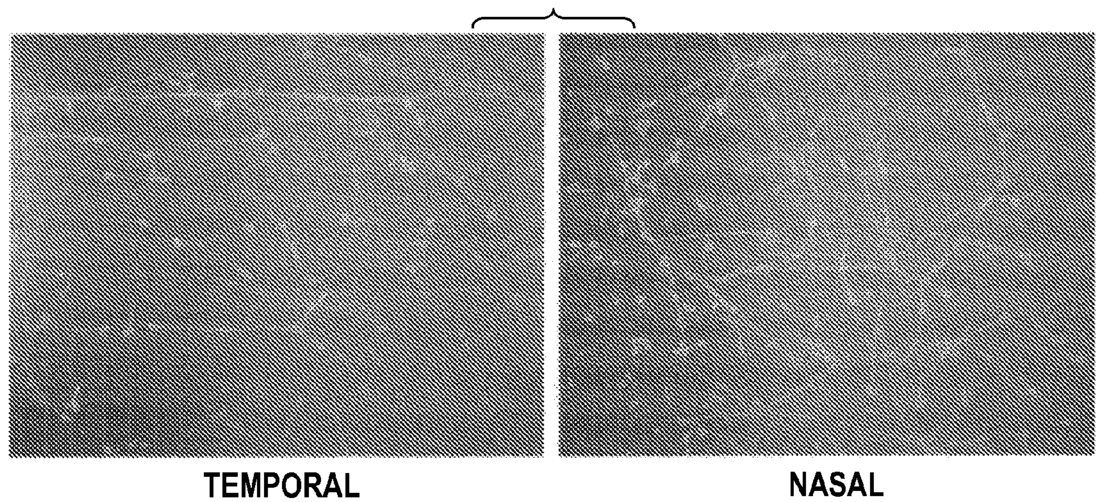
FIG. 1. Neogenin is a high affinity binding site for RGM.

To search for high affinity RGM binding sites in brain, a fusion protein of chick RGM truncated amino terminal to the GPI site was fused to human placental alkaline phosphatase (AP) to express a soluble, carboxy-terminally MycHis tagged secreted protein. When expressed in HEK293 cells, the cRGM-AP fusion protein was processed proteolytically to yield a 110 kDa fusion protein (data not shown). This material retained biological activity as demonstrated by the avoidance of cRGM-AP stripes by temporal retinal ganglion cell axons (FIG. 1A).

Figure 1B:
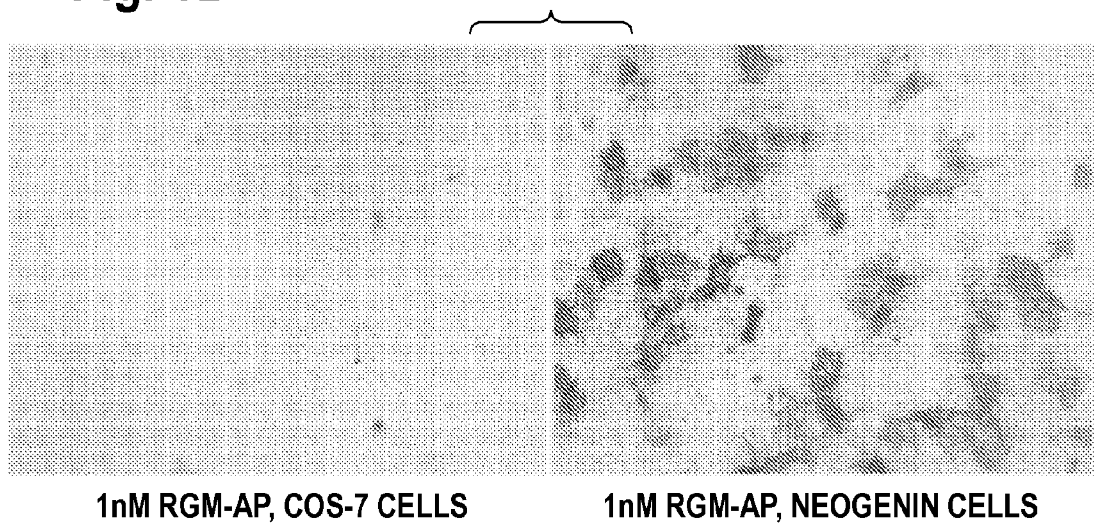
Figure 1C:
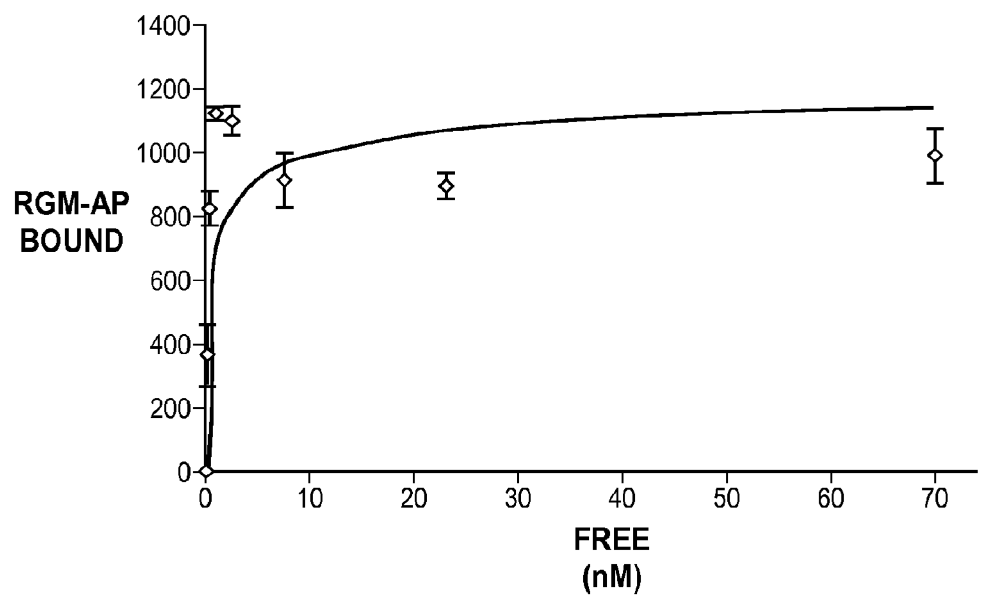
Figure 1D:
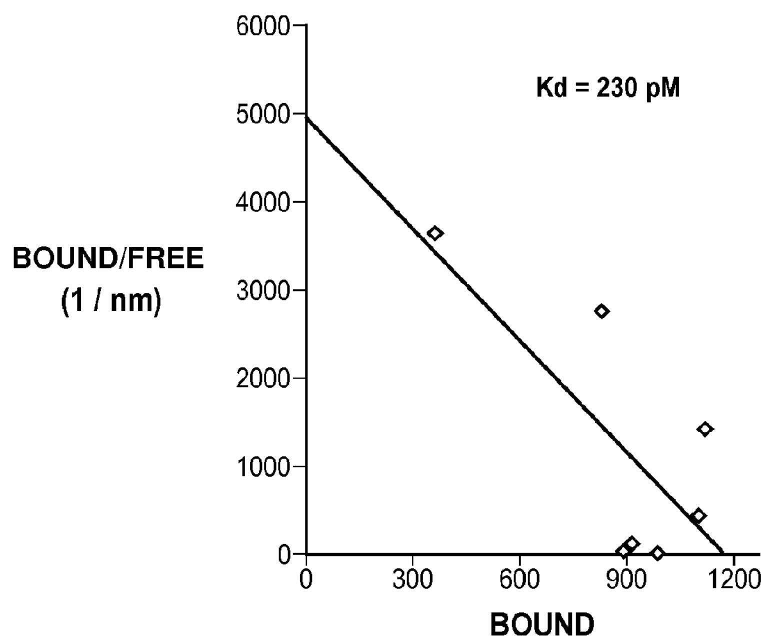
Figure 1E:
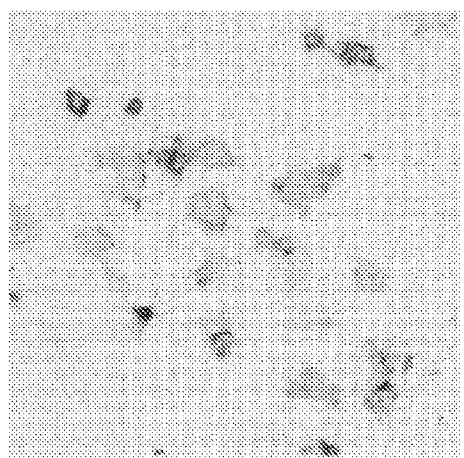
Figure 1E:
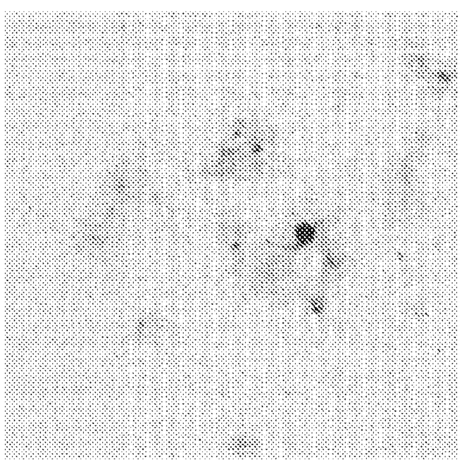
Figure 1E:
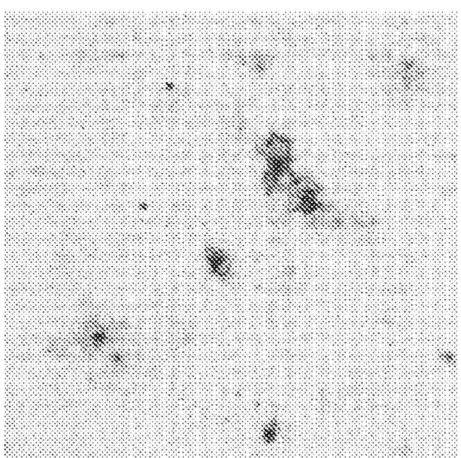

The cRGM-AP fusion protein does not bind to COS-7 kidney-derived cells, so we expressed an adult mouse brain cDNA expression library in these cells and screened for clones driving expression of cell surface binding activity. Only a single clone was identified in screens of 480,000 independent clones. This cDNA clone expressed a saturable binding site for cRGM-AP with a Kd of 230 pM (FIG. 1B-D). DNA sequence analysis revealed that the high affinity RGM-AP binding protein was Neogenin. In the mouse genome there are three RGM-related sequences, that we have termed mRGM-A, mRGM-B and mRGM-C. The three mouse RGM sequences share 41-49% aa identity and 55-61% aa similarity with one another. Chick RGM shares the highest level of identity with mRGM-A at 80% aa identity and 84% aa similarity. Both RGM-A and RGM-B are expressed in many regions of the developing mouse brain, so we tested if AP fusion proteins of these also bind to Neogenin. Both mRGM-A and mRGM-B bind mNeogenin with high affinity (FIG. 1E).

To verify that the RGM interaction with Neogenin was due to their participation in a physical complex, RGM and Neogenin were co-expressed in HEK293T cells and analyzed by co-immunoprecipitation. RGM precipitates contained detectable Neogenin but control immunoprcipitates did not (FIG. 2A). More relevant for in vivo activity, affinity chromatography using the RGM-AP protein isolated Neogenin protein from adult mouse brain tissue (FIG. 2B).

The RGM interaction with Neogenin raises several issues of specificity since Neogenin has been described previously as a Netrin binding protein[4]. RGM and Netrin-1 show no significant sequence similarity[3]. It should be noted that the reported Netrin binding affinity to Neogenin (~2nM) is an order of magnitude less than the RGM affinity (230pM). We considered whether RGM-AP binds to other known Netrin receptors. DCC is most closely related to Neogenin in sequence and the two proteins are reported to have similar affinities for Netrins. Functional studies have demonstrated a role for DCC in mediating axonal guidance by Netrins[6,7], but the role of Neogenin in mediating axonal responses to Netrins have not been documented. DCC has no detectable affinity for RGM-AP, any affinity must be at least 50 fold less than for Neogenin (FIG. 3A). Unc5 proteins can bind Netrin-1 independently of DCC, and serve as obligate co-receptors together with DCC in axon repulsion by Netrins[8]. However, neither Unc5H1 nor Unc5H3 proteins bind RGM-AP (FIG. 3A). Netrin-1 is known to bind to the FNIII region of DCC, rather than the Ig domains[9]. Similarly, full RGM binding affinity is obtained with a truncated Neogenin containing only the FNIII repeats (FIG. 3B). This raises the possibility that RGM and Netrin bind to similar regions of Neogenin. However, the addition of excess Netrin-1 did not appear to alter RGM-AP binding to Neogenin (FIG. 3C). While functional interactions between Netrin and RGM might exist, the two protein do not appear to compete for binding to a single site on Neogenin.

To assess the role of Neogenin binding in RGM signalling in retinal ganglion axons, we purified the soluble recombinant ectodomain of Neogenin via a His tag, and tested its function-blocking capability. To the extent that RGM-Neogenin signalling contributes to retinotectal targeting, the soluble Neogenin ectodomain should disrupt the temporal retinal preference for anterior versus posterior tectal membranes in a stripe assay. The preference of temporal but not nasal retinal ganglion cell axons is obvious in the stripe assay under control conditions (FIG. 4A, C), as reported previously[10,11]. In the presence of soluble Neogenin the preference of temporal axons for anterior tectal stripes is lost (FIG. 4B). Blockade of retinal axon stripe preference is dose-dependent, with essentially complete blockade at 400 nM soluble Neogenin ectodomain (FIG. 4C). The tectum contains an anterior-to-posterior both RGM and ephrin A2/A5 guidance cues[3,5]. To ensure that soluble Neogenin ectodomain was selectively blocking RGM function, and not ephrin function, we tested the ligand binding specificity of these systems (FIG. 4D). It is clear that ephrinA2/5 bind to EphA3 but not Neogenin and that RGM binds to Neogenin but not EphA3. Thus, the blockade of stripe preference by soluble Neogenin demonstrates a crucial role for RGM/Neogenin signalling in determining retinotectal axon guidance in vitro.

RGMs form high affinity complexes with Neogenin and Neogenin/RGM complexes play a significant role in retinotectal guidance systems. Since the Neogenin-related DCC functions as an axonal guidance receptor for Netrin-1, there is precedence for this family of receptor proteins mediating axonal guidance in vivo[6,7]. The interaction of RGM with Neogenin is of higher affinity than Netrin-1's interaction with Neogenin, and is specific amongst Netrin-binding proteins. Thus Neogenin's primary role in nervous system development is as a RGM receptor, with DCC serving as the primary Netrin receptor. It is of interest that both Neogenin and RGM (data not shown) are highly expressed in adult nervous system and in the injured nervous system, thus implicating them in adult neural regeneration. For example, RGM is localized at very high concentrations in brains at the lesion site in humans suffering form traumatic brain injury or from cerebral ischemia From approximately 1-7 days post injury or post cerebral ischemia, monocytes, lymphocytes, granulocytes and a few neurons express RGM. In subsequent stages, RGM is present on fibroblast-like cells, on reactive astrocytes and in fresh and mature scar tissue which forms at the lesion site.

The invention provides methods and compositions for identifying pharmacological agents useful in the diagnosis or treatment of mammalian, particularly human, neurological disease or injury. The methods rely on monitoring the interaction of a mammalian, particularly human, RGM and a corresponding Neogenin in the presence and absence of a candidate agent. A wide variety of assays can be used, including receptor activation assays and binding assays. Binding assays may monitor RGM binding to a domain of or a full-length receptor expressed on a cell, or in vitro protein-protein binding of a RGM to a full length or truncated receptor. In some embodiments, such in vitro screens involve the immobilization of one of the binding partners on a solid substrate.

Typically, these assays involve a mixture comprising an isolated RGM and an isolated Neogenin capable of specifically binding said RGM. We have demonstrated that these mammalian gene products function as natural mammalian, and in particular, human, ligand-receptor complex. The general methods comprise the steps of: (1) forming a mixture comprising an isolated RGM, an isolated negoenin-1 receptor, and a candidate pharmacological agent; (2) incubating said mixture under conditions whereby, but for the presence of said candidate pharmacological agent, said RGM specifically binds said Neogenin at a first binding affinity; and. (3) detecting a second binding affinity of said RGM to said Neogenin, wherein a difference between said first and second binding affinity indicates that said candidate pharmacological agent is a lead compound for a pharmacological agent useful in the diagnosis or treatment of neurological disease or injury.

The term "modulator" as employed herein relates to "inhibitors" as well as "activators" of RGM or Neogenin function. Most preferably said "modulation" is an inhibition, wherein said inhibition may be a partial or a complete inhibition. An inhibitor of RGM, for example, need not bind RGM but might inhibit RGM by interacting with Neogenin and inhibiting the RGM/Neogenin interaction. In addition, the inhibitor could inhibit RGM by inhibiting transcription, translation or processing (pre or post-translational) of RGM. Similarly, a modulator may mimic RGM function through binding to Neogenin without sharing homology to RGM.

The term, RGM amino acid sequence relates to the RGM polypeptides disclosed in WO 02/051438 (to which the following SEQ ID Nos. refer). In particular, SEQ ID NOs: 20 and 21 depict human RGM1. Human RGM1 has been localized on chromosome 15. Further, human RGMs comprise RGM2 and RGM3. RGM2 is depicted in SEQ ID NO: 23 (amino acid sequence) and is encoded by a nucleotide sequence as shown in SEQ ID NO: 22. Human RGM2 has been localized on chromosome 5. Furthermore, human RGM3 is shown in appended SEQ ID NO: 25 (amino acid sequence) and encoded by a nucleotide sequence as depicted in SEQ ID NO: 24. Human RGM3 is located on chromosome 1. Yet, as will be discussed herein below, said term relates also to further RGM homologues.

The term "(poly) peptide" means, in accordance with the present invention, a peptide, a protein, or a (poly) peptide which encompasses amino acid chains of a given length, wherein the amino acid residues are linked by covalent peptide bonds. However, peptidomimetics of such RGM proteins/(poly) peptides or Neogenin proteins/(poly)peptides wherein amino acid (s) and/or peptide bond (s) have been replaced by functional analogs are also encompassed by the invention.

The present invention is not restricted to uses of RGM and Neogenin from human, mouse or chicken and its inhibitors but also relates to the use of inhibitors of RGM and Neogenin or of RGM and Neogenin itself (or functional fragments or derivatives thereof) from other species. Since the present invention provides for the use of amino acid sequences/polypeptides of RGM and Neogenin and their corresponding inhibitors and since the amino acid sequences of human and chicken RGM and Neogenin have been disclosed, the person skilled in the art is provided with the information to obtain RGM and Neogenin sequences from other species, like, inter alia, mouse, rat, pig, etc. The relevant methods are known in the art and may be carried out by standard methods, employing, inter alia, degenerate and non degenerate primers in PCR-techniques.

Basic molecular biology methods are well known in the art and, e.g., described in Sambrook (Molecular Cloning; A Laboratory Manual, 2nd Edition, Cold Spring Harbor Laboratory Press, Cold Spring Harbor, N.Y. (1989)) and Ausubel, "Current Protocols in Molecular Biology", Green Publishing Associates; and Wiley Interscience, N.Y. (1989).

Furthermore, as employed in the context of the present invention, the terms "RGM", "RGM modulator", "RGM-inhibitor", "Neogenin", "Neogenin modulator" and "Neogenin inhibitor" also relate to RGM and Neogenin molecules (and their corresponding inhibitors) which are variants or homologs of the RGM and Neogenin molecules (and their inhibitors) as described herein. "Homology" in this context is understood to refer in this context to a sequence identity of RGM and Neogenin of at least 70%, preferably more than 80% and still more preferably more than 90% on the amino acid level. The present invention, however, comprises also (poly)peptides deviating from wildtype amino acid sequences of human or chicken RGM and Neogenin, wherein said deviation may be, for example, the result of amino acid and/or nucleotide substitution(s), deletion(s), addition(s), insertion(s), duplication(s), inversion(s) and/or recombination(s) either alone or in combination. Those deviations may naturally occur or be produced via recombinant DNA techniques well known in the art. The term "variation" as employed herein also comprises "allelic variants". These allelic variations may be naturally occurring allelic variants, splice variants as well as synthetically produced or genetically engineered variants.

FIGS. 5 and 6 present the amino acid sequence and nucleotide sequence, respectively, for Neogenin. For the purposes of this application, reference to "wildtype" Neogenin refers to this sequence although, as described herein, significant modifications of this sequence will not depart from the spirit of the invention. To the extent that allelic or other differences occur among Neogenin genes, these differences may be used to create specific probes or antibodies.

The term "polynucleotide" in accordance with the present invention comprises coding and, wherever applicable, non-coding sequences (like promoters, enhancers etc.). It comprises DNA, RNA as well as PNA. In accordance with the present invention, the term "polynucleotide/nucleic acid molecule" comprises also any feasible derivative of a nucleic acid to which a nucleic acid probe may hybridize. Said nucleic acid probe itself may be a derivative of a nucleic acid molecule capable of hybridizing to said nucleic acid molecule or said derivative thereof. The term "nucleic acid molecule" further comprises peptide nucleic acids (PNAs) containing DNA analogs with amide backbone linkages (Nielsen, Science 254 (1991), 1497-1500). The term "nucleic acid molecule" which encodes a RGM (poly) peptide or a functional fragment/derivative thereof, in connection with the present invention, is defined either by (a) the specific nucleic acid sequences encoding said (poly) peptide specified in the present invention or (b) by nucleic acid sequences hybridizing under stringent conditions to the complementary strand of the nucleotide sequences of (a) and encoding a (poly) peptide deviating from the nucleic acid of (a) by one or more nucleotide substitutions, deletions, additions or inversions and wherein the nucleotide sequence shows at least 70%, more preferably at least 80% identity with the nucleotide sequence of said encoded RGM and Neogenin (poly)peptides having an amino acid sequence as defined herein and functions as a RGM or Neogenin (or a functional fragment/derivative thereof) as the case may be.

The term "modulator" as employed herein also comprises the term "inhibitor", as mentioned herein above. The term comprises "modulators" of the RGM and Neogenin polypeptides and/or the RGM and Neogenin encoding nucleic acid molecule/genes. In context of this invention it is-also envisaged that said "modulation" may lead, when desired, to an activation of RGM and/or Neogenin.

The term "functional fragment or derivative thereof" in context of the present invention and in relation to the RGM and Neogenin molecules comprises fragments of the RGM and Neogenin molecules defined herein having a length of at least 10, in another embodiment 25, in another embodiment at least 50, in another embodiment at least 75, and in another embodiment at least 100 amino acids depending on the application as would be known to one of skill in the art.

Functional fragments of the herein identified RGM and Neogenin molecules or RGM and Neogenin molecules of other species (homologous RGM and Neogenin) may be comprised in fusion and/or chimeric proteins. "Functional fragments" comprise RGM or Neogenin fragments (or their encoding nucleic acid molecules) which are able to replace RGM or Neogenin full length molecules in corresponding assays (as disclosed in, e. g. collapse and/or stripe assays) or may elucidate an anti-RGM or anti-Neogenin specific immune-response and/or lead to specific anti-RGM or anti-Neogenin antibodies. An example of such a "functional fragment" would be a fragment of RGM capable of binding Neogenin. In context of the present invention, polynucleotides encoding functional fragments of RGM or Neogenin and/or their derivatives have at least 15, in another embodiment at least 30, in another embodiment at least 90, in another embodiment at least 150, and in another embodiment at least 300 nucleotides depending on the application as would be known to one of skill in the art.

The term "derivative" means in context of their invention derivatives of RGM and Neogenin molecules and/or their encoding nucleic acid molecules and refer to natural derivatives (like allelic variants) as well as recombinantly produced derivatives/variants which may differ from RGM or Neogenin molecules by at least one modification/mutation, e. g. at least one deletion, substitution, addition, inversion or duplication. The term "derivative" also comprises chemical modifications. The term "derivative" as employed herein in context of the RGM and Neogenin molecule also comprises soluble RGM and Neogenin molecules which do not comprise any membrane anchorage.

As mentioned herein above, the present invention provides for the use of a modulator, preferably an inhibitor, of RGM molecules and/or their corresponding encoding polynucleotides/nucleic acid molecules for the preparation of a pharmaceutical composition for preventing, alleviating or treating various disorders of the nervous system, angiogenic disorders or disorders of the cardio-vascular system and malignancies of different etiology.

In a preferred embodiment, said disorders of the nervous system comprise degeneration or injury of vertebrate nervous tissue, in particular neurodegenerative diseases, nerve fiber injuries and disorders related to nerve fiber losses.

Said neurodegenerative diseases may be selected from the group consisting of motorneuronal diseases (MND), amyotrophic lateral sclerosis (ALS), Alzheimer disease, Parkinsons disease, progressive bulbar palsy, progressive muscular atrophy, HIV-related dementia and spinal muscular atrophy (ies), Down's Syndrome, Huntington's Disease, Creutzfeldt-Jacob Disease, Gerstmann-Straeussler Syndrome, kuru, Scrapie, transmissible mink encephalopathy, other unknown prion diseases, multiple system atrophy, Riley-Day familial dysautonomia said nerve fiber injuries may be selected from the group consisting of spinal cord injury(ies), brain injuries related to raised intracranial pressure, trauma, secondary damage due to increased intracranial pressure, infection, infarction, exposure to toxic agents, malignancy and paraneoplastic syndromes and wherein said disorders related to nerve fiber losses may be selected from the group consisting of paresis of nervus facials, nervus medianus, nervus ulnaris, nervus axillaris, nervus thoracicus longus, nervus radialis and for of other peripheral nerves, and other aquired and non-aquired deseases of the (human) central and peripheral nervous system.

The above mentioned spinal cord and brain injuries not only comprise traumatic injuries but also relate to injuries caused by stroke, ischemia and the like. It is in particular envisaged that the inhibitors as defined herein below and comprising, inter alia, anti-RGM antibodies be employed in the medical art to stimulate nerve fiber growth in individuals, in particular in vertebrates, most preferably in humans.

In a more preferred embodiment of the present invention, the invention provides for the use of a modulator, preferably an inhibitor to RGM (or a functional fragment or derivative thereof) for the preparation of a pharmaceutical composition for the treatment of disorders of the cardio-vascular system, wherein these disorders, e. g., comprise disorders of the blood-brain barrier, brain oedema, secondary brain damages due to increased intracranial pressure, infection, infarction, ischemia, hypoxia, hypoglycemia, exposure to toxic agents, malignancy, paraneoplastic syndromes.

It is envisaged, without being bound by theory, that RGM inhibitors may stimulate or allow surviving neurons to project collateral fibers into the diseased tissue, e. g. the ischemic tissue.

RGM is expressed locally at the side of artificial transection of brain/spinal cord tissue in test animals (like rats), e. g., in the penumbra region surrounding an ischemic core of a human suffering focal ischemia in the temporal cortex. Furthermore, it is documented in the that RGM is, surprisingly, expressed in tissue(s) affected by traumatic brain injuries.

The invention also relates to the use of a RGM polypeptide or a functional fragment or derivative thereof or the use of a polynucleotide encoding the same (polypeptides and polynucleotides as defined herein), wherein the above described disease or condition associated with seizures is epilepsy. An epilepsy is thereby characterized by an epileptic seizure as a convulsion or transient abnormal event experienced by the subject, e. g. a human patient, due to a paroxysmal discharge of (cerebral) neurons. The epileptic seizures comprise tonic seizures, tonic-clonic seizures (grand mal), myoclonic seizures, absence seizures as well as akinetic seizures. Yet, also comprised are in context of this invention simple partial seizures, e. g. Jacksonian seizures and seizures due to perinatal trauma and/or fetal anoxia. As mentioned herein below, the uses described herein relate in particular to the preparation of pharmaceutical compositions for the treatment of diseases/conditions associated with aberrant sprouting of nerve fibers, like epilepsy; see also Routbort, Neuroscience 94 (1999), 755-765.

In a even more preferred embodiment of the invention, the modulator, preferably the inhibitor of RGM (or of its functional fragment or derivative thereof or of its encoding nucleic acid molecule) is used for the preparation of a pharmaceutical composition for the modification of neovascularization. Said modification may comprise activation as well as stimulation. It is in particular envisaged that said neovascularisation be stimulated and/or activated in diseased tissue, like inter alia, ischemic and/or infarctious tissue. Furthermore, it is envisaged that the RGM-inhibitors described herein may be employed in the regulation of the blood-brain barrier permeability.

It is furthermore envisaged that said modulators, preferably said inhibitors for RGM be employed in the alleviation, prevention and/or inhibition of progression of vascular plaque formation (e. g. artherosclerosis) in cardio-vascular, cerebo-vascular and/or nephrovascular diseases/disorders.

Furthermore, the present invention provides for the use of a modulator, preferably an inhibitor of RGM as defined herein for the preparation of a pharmaceutical composition for remyelination. Therefore, the present invention provides for a pharmaceutical composition for the treatment of demyelinating diseases of the CNS, like multiple sclerosis or of demyelinating diseases like peripheral neuropathy caused by diphteria toxin, Landry-Guillain-Barre-Syndrom, Elsberg-Syndrom, Charcot-Marie-Tooth disease and other polyneuropatias. A particular preferred inhibitor of RGM in this context is an antibody directed against RGM, e.g. an IgM antibody. It has previously be shown that certain IgMs bind to oligodendrocytes and thereby induce remyelination. IgM antibodies against RGM are known in the art and comprise e.g. the F3D4 described in the appended examples.

In addition the invention provides for the use of a RGM polypeptide as defined herein or of a functional fragment or derivative thereof or of a polynucleotide encoding said polypeptide or fragment or derivative for the preparation of a pharmaceutical composition for preventing, alleviating or treating diseases or conditions associated with the activity of autoreactive immune cells or with overactive inflammatory cells.

Most preferably these cells are T-cells.

Furthermore, the present invention relates to the use of a modulator, preferably an inhibitor or another RGM binding molecule of a RGM polypeptide or of a functional fragment or derivative thereof or of a polynucleotide encoding said polypeptide or of fragment/derivative thereof for modifying and/or altering the differentiation status of neuronal stem cells and/or their progenitors. Said stem cells are normally found in the subventricular zones of many brain regions. It is known that factors in the microenvironment of the brain dramatically influence the differentiation of undifferentiated stem cells. It is assumed that due to the characteristic expression of RGM in the subventricular layers of many different brain regions, this molecule could be a marker for stem cells. Furthermore, RGM inhibitors, like antibodies could be useful markers for stem cells. Most important in stem cell biology is the understanding of factors influencing their differentiation. It is therefore assumed that RGM inhibitors change the developmental fate of these cells.

RGM is not only expressed in ischemic tissue but is also expressed in scar tissue surrounding (brain) lesions.

It is particularly preferred that the modulator, preferably the inhibitor of the RGM molecule (or its functional fragment or derivative) is an antibody or a fragment or a derivative thereof, is an aptamer, is a specific receptor molecule capable of interacting with a RGM polypeptide or with a functional fragment or derivative thereof, or is a specific nucleic acid molecule interacting with a polynucleotide encoding an RGM and/or the polypeptide.

The antibody to be used in context of the present invention can be, for example, polyclonal or monoclonal antibodies. Techniques for the production of antibodies are well known in the art and described, e. g. in Harlow and Lane "Antibodies, A Laboratory Manual", CSH Press, Cold Spring Harbor, 1988. The production of specific anti-RGM antibodies is further known in the art (see, e. g. Mutter (1996) loc. cit.) or described in the appended examples.

The term "antibody" as employed herein also comprises chimeric, single chain and humanized antibodies, as well as antibody fragments, like, inter alia, Fab fragments.

Antibody fragments or derivatives further comprise F(ab') 2, Fv or scFv fragments; see, for example, Harlow and Lane, loc. cit. Various procedures are known in the art and may be used for the production of such antibodies and/or fragments, see also appended examples. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide (s) of this invention. Also, transgenic animals may be used to express humanized antibodies to polypeptides of this invention. Most preferably, the antibody to be used in the invention is a monoclonal antibody, for example the F3D4 antibody described in the appended examples may be employed when an IgM is desired. The general methodology for producing, monoclonal antibodies is well-known and has been described in, for example, Kohler and Milstein, Nature 256 (1975), 494-496 and reviewed in J. G. R. Hurrel, ed., "Monoclonal Hybridoma Antibodies: Techniques and Applications", CRC Press Inc., Boco Raron, Fla. (1982), as well as that taught by L. T. Mimms et al., Virology 176 (1990), 604-619.

Preferably, said antibodies (or inhibitors) are directed against functional fragments of the RGM polypeptide. As pointed out herein above and as documented in the appended examples, such functional fragments are easily deducible for the person skilled in the art and, correspondingly, relevant antibodies (or other inhibitors) may be produced.

The "modulator", preferably the "inhibitor" as defined herein may also be an aptamer.

In the context of the present invention, the term "aptamer" comprises nucleic acids such as RNA, ssDNA (ss=single stranded), modified RNA, modified ssDNA or PNAs which bind a plurality of target sequences having a high specificity and affinity.

Aptamers are well known in the art and, inter alia, described in Famulok, Curr. Op. Chem. Biol. 2 (1998), 320-327. The preparation of aptamers is well known in the art and may involve, inter alia, the use of combinatorial RNA libraries to identify binding sites (Gold, Ann. Rev. Biochem. 64 (1995), 763-797). Said other receptors may, for example, be derived from said antibody etc. by peptidomimetics.

Other specific "receptor" molecules which may function as inhibitors of the RGM polypeptides are also comprised in this invention. Said specific receptors may be deduced by methods known in the art and comprise binding assays and/or interaction assays. These may, inter alia, involve assays in the ELISA-format or FRET-format.

Said "inhibitor" may also comprise specific peptides binding to and/or interfering with RGM.

Furthermore, the above recited "modulator", preferably "inhibitor" may function at the level of RGM gene expression. Therefore, the inhibitor may be a (specific) nucleic acid molecule interacting with a polynucleotide encoding a RGM molecule (or a functional fragment or derivative thereof.) These inhibitors may, e. g., comprise anti sense nucleic acid molecules, small inhibitory RNAs (siRNAs) or ribozymes.

The nucleic acid molecule encoding RGM or Neogenin may be employed to construct appropriate anti-sense oligonucleotides or siRNA molecules.

Said anti-sense oligonucleotides are able to inhibit the function of wild-type (or mutant) RGM and Neogenin genes and comprise, for example, at least 15 nucleotides, at least 20 nucleotides, at least 30 nucleotides or at least 40 nucleotides.

In addition, ribozyme approaches are also envisaged for use in this invention.

Ribozymes may specifically cleave the nucleic acid molecule encoding RGM or Neogenin.

In the context of the present invention ribozymes comprise, inter alia, hammerhead ribozymes, hammerhead ribozymes with altered core sequences or deoxyribozymes (see, e. g., Santoro, Proc. Natl. Acad. Sci. USA 94 (1997), 4262) and may comprise natural and in vitro selected and/or synthesized ribozymes.

Nucleic acid molecules according to the present invention which are complementary to nucleic acid molecules coding for proteins/ (poly) peptides regulating, causing or contributing to obesity and/or encoding a mammalian (poly) peptide involved in the regulation of body weight (see herein below) may be used for the construction of appropriate ribozymes (see, e. g., EP-B1 0 291 533, EP-A1 0 321 201, EP-A2 0 360 257) which specifically cleave nucleic acid molecules of the invention. Selection of the appropriate target sites and corresponding ribozymes can be done as described for example in Steinecke, Ribozymes, Methods in Cell Biology 50, Galbraith, eds. Academic Press, Inc. (1995), 449-460.

Said "inhibitor" may also comprise double-stranded RNAs, which lead to RNA mediated gene interference (see Sharp, Genes and Dev. 13 (1999), 139-141). Further potential inhibitors of RGM or Neogenin may be found and/or deduced by interaction assay and employing corresponding read-out systems. These are known in the art and comprise, inter alia, two hybrid screenings (as, described, inter alia, in EP-0 963 376, WO 98/25947, WO 00/02911), GST-pull-down columns, co-precipitation assays from cell extracts as described, inter alia, in Kasus-Jacobi, Oncogene 19 (2000), 20522059, "interaction-trap" systems (as described, inter alia, in U.S. Pat. No. 6,004,746), expression cloning (e. g. lambda gt11), phage display (as described, inter alia, in U.S. Pat. No. 5,541, 109), in vitro binding assays and the like. Further interaction assay methods and corresponding read out systems are, inter alia, described in U.S. Pat. No. 5,525,490, WO 99/51741, WO 00/17221, WO 00/14271 or WO 00/05410.

In yet another embodiment, the present invention provides for the use of the RGM amino acid sequence or of a functional fragment or derivative thereof or of a polynucleotide encoding said polypeptide or fragment or derivative for the preparation of a pharmaceutical composition for preventing or treating tumor growth or formation of tumor metastases.

RGM (naturally isolated or recombinantly produced) and/or functional fragments thereof may be employed for the preparation of a pharmaceutical composition for the treatment of neoplastic disorders, in particular of disorders related to tumor (cell) migration, metastasis and/or tumor invasion. Furthermore, it is envisaged that RGM inhibits undesired neovascularisation. Said neovascularisation, as an angiogenic disorder during neoplastic events, should be prevented in order to limit, inter alia, tumor growth.

Growth cones of neurons and (invasive) tumor cells secrete a cocktail of proteases (uPA, tPA, MNPs, etc.) in order to degrade extracellular matrix. Furthermore, similar mechanisms for adhesion and (cell) migration are employed by these cellular systems. RGM and/or its functional fragments may be employed to actively stimulate withdrawal of lamellipodia of tumor cells and/or to induce their collapse.

In addition the invention provides for the use of a RGM polypeptide as defined herein or of a functional fragment or derivative thereof or of a polynucleotide encoding said polypeptide or fragment or derivative for the preparation of a pharmaceutical composition for preventing, alleviating or treating diseases or conditions associated with the activity of autoreactive immune cells or with overactive inflammatory cells.

Most preferably these cells are T-cells.

In yet another embodiment, the invention provides for the use of a the RGM polypeptide h or of a functional fragment or derivative thereof or of a polynucleotide encoding said polypeptide or fragment or derivative for the preparation of a pharmaceutical composition for the treatment of inflammation processes and/or allergies, for wound healing or for the suppression/alleviation of scar formation. Scar tissue is formed by invading cells, most importantly by fibroblasts and/or glial cells. Migration and adhesion of these cells are required to get to the lesion side. RGM or an active fragment/derivative could prevent accumulation of these cells in the lesion side, thereby preventing or slowing down scar formation. In inflammatory reactions cells migrate to the inflamed region and RGM or its active fragment/derivative prevent or reduce migration of these cells to the side of inflammation, thereby preventing overactive inflammatory reactions.

In context of the present invention, the term "pharmaceutical composition" also comprises optionally further comprising an acceptable carrier and/or diluent and/or excipient. The pharmaceutical composition of the present invention may be particularly useful in preventing and/or treating pathological disorders in vertebrates, like humans. Said pathological disorders comprise, but are not limited to, neurological, neurodegenerative and/or neoplastic disorders as well as disorders associated with seizures, e. g. epilepsy. These disorders comprise, inter alia, Alzheimer's disease, Parkinson's disease, amyotrophic lateral sclerosis (FALS/SALS), ischemia, stroke, epilepsy, AIDS dementia and cancer.

The pharmaceutical composition may also be used for prophylactic purposes.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose.

Administration of the suitable compositions may be effected by different ways, e. g., by intravenous, intraperitoneal, subcutaneous, intramuscular, topical, intradermal, intranasal or intrabronchial administration. However, it is also envisaged that the pharmaceutical compositions are directly applied to the nervous tissue. The dosage regimen will be determined by the attending physician and clinical factors. As is well known in the medical arts, dosages for any one patient depends upon many factors, including the patient's size, body surface area, general health, age, sex, the particular compound to be administered, time and route of administration, and other drugs being administered concurrently. Pharmaceutical active matter may be present preferably, inter alia, in amounts between 1 ng and 1000 mg per dose, more preferably in amounts of 1 ng to 100 mg however, doses below or above this exemplary range are envisioned, especially considering the aforementioned factors. If the regimen is a continuous infusion, it should also be in the range of 1 ug to 10 mg units per kilogram of body weight per minute, respectively. Progress can be monitored by periodic assessment. The compositions of the invention may be administered locally or systemically. Administration will generally be parenterally, e. g., intravenously. The compositions of the invention may also be administered directly to the target site, e. g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents, depending on the intended use of the pharmaceutical composition. Such agents may be drugs acting on the central nervous system as well as on small, unmyelinated sensory nerve terminals (like in the skin), neurons of the peripheral nervous system of the digestive tract., etc.

It is also understood that the pharmaceutical composition as defined herein may comprise nucleic acid molecules encoding RGM and Neogenin (and/or functional fragments or derivatives thereof) or corresponding RGM and Neogenin inhibitors as defined herein. As mentioned herein-above, said inhibitors comprise, but are not limited to, antibodies, aptamer, RGM-interacting peptides as well as inhibitors interacting with the RGM-encoding polynucleotides.

Accordingly, the present invention also provides for a method of treating, preventing and/or alleviating pathological disorders and conditions as defined herein, whereby said method comprises administering to a subject in need of such a treatment a pharmaceutical composition/medicament as defined herein. Preferably, said subject is a human.

The nucleic acid molecules may be particularly useful in gene therapy approaches and may comprise DNA, RNA as well as PNA. Said nucleic acid molecules may be comprised in suitable vectors, either inter alia, gene expression vectors. Such a vector may be, e. g., a plasmid, cosmid, virus, bacteriophage or another vector used e. g. conventionally in genetic engineering, and may comprise further genes such as marker genes which allow for the selection of said vector in a suitable host cell and under suitable conditions.

Furthermore, the vectors may, in addition to the nucleic acid sequences encoding RGM and Neogenin or the corresponding inhibitors, comprise expression control elements, allowing proper expression of the coding regions in suitable host cells or tissues.

Such control elements are known to the artisan and may include a promoter, translation initiation codon, translation and insertion site for introducing an insert into the vector. Preferably, the nucleic acid molecule of the invention is operatively linked to said expression control sequences allowing expression in (eukaryotic) cells. Particularly preferred are in this context control sequences which allow for correct expression in neuronal cells and/or cells derived from nervous tissue.

Control elements ensuring expression in eukaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor la-promoter, CMV enhancer, CaM-kinase promoter or SV40-enhancer. For the expression for example in nervous tissue and/or cells derived therefrom, several regulatory sequences are well known in the art, like the minimal promoter sequence of human neurofilament L (Charron, J. Biol. Chem 270 (1995), 25739-25745). Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 Pharmacia), pRc/CMV, pcDNA1, pcDNA3 (In-Vitrogene, as used, inter alia in the appended examples), pSPORT1 (GIBCO BRL) or pGEMHE Promega). Beside the nucleic acid molecules defined herein, the vector may further comprise nucleic acid sequences encoding for secretion signals. Such sequences are well known to the person skilled in the art. Furthermore, depending on the expression system used leader sequences capable of directing the protein/(poly) peptide to a cellular compartment may be added to the coding sequence of the nucleic acid molecules of the invention and are well known in the art. The leader sequence (s) is (are) assembled in appropriate phase with translation, initiation and termination sequences, and preferably, a leader sequence capable of directing secretion of translated protein, or a part thereof.

As mentioned herein above, said vector may also be, besides an expression vector, a gene transfer and/or gene targeting vector. Gene therapy, which is based on introducing therapeutic genes into cells by ex-vivo or in-vivo techniques is one of the most important applications of gene transfer. Suitable vectors, vector systems and methods for in-vitro or in-vivo gene therapy are described in the literature and are known to the person skilled in the art; see, e. g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957, Schaper, Current Opinion in Biotechnology 7 (1996), 635-640 Verma, Nature 389 (1997), 239-242 WO 94/29469, WO 97/00957, U.S. Pat. Nos. 5,580,859, 589,66 or 4,394,448 and references cited therein.

In particular, said vectors and/or gene delivery systems are also described in gene therapy approaches in neurological tissue/cells (see, inter alia Blomer, J. Virology 71 (1997) 6641-6649) or in the hypothalamus (see, inter alia, Geddes, Front Neuroendocrinol. 20 (1999), 296-316 or Geddes, Nat. Med. 3 (1997), 1402-1404).

Further suitable gene therapy constructs for use in neurological cells/tissues are known in the art, for example in Meier (1999), J. Neuropathol. Exp. Neurol. 58,10991110. The nucleic acid molecules and vectors of the invention may be designed for direct introduction or for introduction via liposomes, viral vectors (e. g. adenoviral, retroviral), electroporation, ballistic (e. g. gene gun) or other delivery systems into the cell. Additionally, a baculoviral system can be used as eukaryotic expression system for the nucleic acid molecules described herein.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i. e. arresting its development; or (c) relieving the disease, i. e. causing regression of the disease.

In yet another embodiment, the present invention provides for the use of a RGM or Neogenin polypeptide or of a functional fragment or derivative thereof or of a polynucleotide encoding said polypeptide or fragment or derivative as a marker of stem cells. Since it is envisaged that stem cells as well as their undifferentiated progenitor cells express RGM and Neogenin, RGM and Neogenin (and/or functional fragments or derivatives thereof) may be employed to influence the differentiation/differentiation pattern of said stem cells.

It is furthermore envisaged that antibodies directed against RGM or Neogenin or functional fragment(s)/derivative(s) thereof may be employed to influence the differentiation of (neuronal) stem cells and (neuronal) progenitor cells. It is particularly preferred that said antibodies (as well as other RGM-inhibitors and/or RGM-binding molecules) be employed to selectively label stem cells. Therefore these reagents may be employed as markers for stem cells. It is also envisaged that peptides or derivatives be employed in said purpose.

In a particularly preferred embodiment of the present invention, the polypeptide and/or fragment thereof which comprises or has an RGM amino acid sequence to be used in accordance with their invention is a soluble, i. e. not membrane bound molecule.

As shown in Davis (1994), Science 266,816-819, ephrins, in particular A-ephrins, are not active in soluble, monomeric form. In contrast, soluble RGMs are active and may function without any membrane-attachment. RGM, in contrast to ephrins, is capable of self-formation of dimers and/or of the formation of higher aggregates. The invention also provides for the use of a RGM molecule or functional fragment or derivative thereof or of a polynucleotide encoding said polypeptide or a fragment or a derivative for the preparation of a pharmaceutical composition for alleviating, preventing and/or treating homeostatic and/or bleeding disorders and/or vascular damage.

It is envisaged, without being bound by theory, that RGMs may, due to their structural homology to von-Willebrand factor (vWF), be employed in the treatment of said disorders/diseases. Furthermore, it is envisaged that RGM may interact with von Willebrand factor and that said molecule, thereby, influences the activity of vWF.

Furthermore, the inhibitors as defined herein should be employed in disorders where immune cells invade the brain, like multiple sclerosis, encephalomyelitis disseminata.

The present invention also provides for the use of an antibody or a fragment or a derivative thereof, or an aptamer, or a binding molecule capable of interacting with a polypeptide having or comprising the RGM or Neogenin amino acid sequence or with functional fragment or derivative thereof or of a nucleic acid molecule capable of interacting with a polynucleotide encoding said polypeptide or a fragment thereof for the preparation of a diagnostic composition for detecting neurological and/or neurodegenerative disorders or dispositions thereto.

The diagnostic composition may be used, inter alia, for methods for determining the expression of the nucleic acids encoding RGM and Neogenin polypeptides by detecting, inter alia, the presence of the corresponding mRNA which comprises isolation of RNA from a cell, contacting the RNA so obtained with a nucleic acid probe as described above under hybridizing conditions, and detecting the presence of mRNAs hybridized to the probe.

Furthermore, corresponding mutations and/or alterations may be detected.

Furthermore, RGM and Neogenin (poly) peptides can be detected with methods known in the art, which comprise, inter alia, immunological methods, like, ELISA or Western blotting.

The diagnostic composition of the invention may be useful, inter alia, in detecting the prevalence, the onset or the progress of a disease related to the aberrant expression of a RGM or Neogenin polypeptide. Accordingly, the diagnostic composition of the invention may be used, inter alia, for assessing the prevalence, the onset and/or the disease status of neurological, neurodegenerative and/or inflammatory disorders, as defined herein above. It is also contemplated that anti-RGM or anti-Neogenin antibodies, aptamers etc. and compositions comprising such antibodies, aptamers, etc. may be useful in discriminating the stage(s) of a disease.

The diagnostic composition optionally comprises suitable means for detection. The nucleic acid molecule(s), vector(s), antibody(ies), (poly)peptide(s), described above are, for example, suitable for use in immunoassays in which they can be utilized in liquid phase or bound to a solid phase carrier. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing nucleic acid molecule(s), vector(s), host(s), antibody(ies), (poly)peptide(s), fusion protein(s) etc. on solid phases include but are not limited to ionic, hydrophobic, covalent interactions and the like. Examples of immunoassays which can utilize said compounds of the invention are competitive and non-competitive immunoassays in either a direct or indirect format. Commonly used detection assays can comprise radioisotopic or non-radioisotopic methods.

Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immuno Assay), FIA fluorescent immune Assay), and CLIA (Chemioluminescent Immune Assay).

Furthermore, the diagnostic compounds of the present invention may be are employed in techniques like FRET (Fluorescence Resonance Energy Transfer) assays.

The nucleic acid sequences encoding RGMs of other species as well as variants of RGMs are easily deducible from the information provided herein. These nucleic acid sequences are particularly useful, as pointed out herein above, in medical and/or diagnostic setting, but they also provide for important research tools. These tools may be employed, inter alia, for the generation of transgenic animals which overexpress or suppress RGMs or wherein the RGM gene is silenced and/or deleted. Furthermore, said sequences may be employed to detect and/or elucidate RGM interaction partners and/or molecules binding to and/or interfering with RGMs. The same holds true for nucleic acid sequences encoding Neogenin.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following Examples are offered by way of illustration and not by way of limitation:

EXAMPLES

Example 1

An expression vector containing a vector-derived signal sequence, the chick RGM sequence from aa 28 to 403 fused to AP and a Myc His tag was constructed. This plasmid was stably transfected into HEK293 cells and secreted RGM-AP protein was purified on a Ni-containing resin. Quantitative binding assays to transfected COS-7 cells were conducted as described for Nogo-AP binding[13]. To isolate a cDNA encoding a chick RGM-AP binding protein, a mouse adult brain cDNA library (Origene) was screened with 10 nM RGM-AP, as described previously for Nogo-66-AP[13]. Mouse RGM-1-AP (Accession number BC023870) and RGM-2-AP (AK080819) were prepared by identical methods as for chick RGM-AP. Mouse RGM-3 is encoded by BC022603. The mouse Unc5H1 and Unc5H3 expression plasmids were derived from EST clones (BI818609 and BI769500) and the pCMV-SPORT6 vector. Truncated versions of chick Neogenin-1 were expressed using the pcDNA3.1-MycHis vector. The soluble ectodomain protein contains aa residues 1-1027 of chick Neogenin-1, the ecto+TM protein contains residues 1-1115 and the 6×FNIII+TM protein contains aa 400-11.15.

A rabbit anti-mouse neogenin-1 antibody was emploed for immunoblots (Santa Cruz Biotechnology, Inc.).

Chick retinal axons and tectal membranes were prepared for stripe assays as described[10,11]. Soluble ectodomain of chick Neogenin-1 (1-1027) was expressed with a carboxyl MycHis tag as a secreted protein in HEK293 cells and purified on a Ni containing resin. Dialyzed protein was added to the stripe assay cultures. Recombinant RGM-AP-MycHis and ephrinA2-Fc or ephrinA5-Fc stripes were prepared using an initial coating of poly-L-lysine coated coverslips with anti-Myc antibody or anti-Human IgG antibody as described for other proteins[10,11,14].

Example 2

Ligand Screening of Transfected COS Cells.

I. Prepare the Ligand

Expression Construct: cDNA encoding the targeted RGM is tagged with the Fc—portion of human IgG and subcloned into a 293 expression vector (pCEP4: In Vitrogen).

Transfection: 293 EBNA cells are transfected (CaPO.sub.4 method) with the RGM expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000.times.g for 10 minutes. The supernatant is filtered (0.45 um) and stored with 0.1% azide at 4.degree. C. for no more than 2 weeks.

II. Prepare Truncated Receptor (Positive Control)

Expression Construct: cDNA encoding a corresponding Neogenin deletion mutant comprising the extracellular domain (truncated immediately N-terminal to the transmembrane region) is subcloned into a 293 expression vector (pCEP4: In Vitrogen).

Transfection: 293 EBNA cells are transfected (CaPO.sub.4 method) with the receptor mutant expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000.times.g for 10 minutes. The supernatant is filtered (0.45 um) and stored with 0.1% azide at 4.degree. C. for no more than 2 weeks.

III. Transfect COS Cells

Seed COS cells (250,000) on 35 mm dishes in 2 ml DME/10% FCS. 18-24 h later, dilute 1 ug of netrin receptor-encoding DNA (cDNA cloned into pMT21 expression vector) into 200 ul serum-free media and add 6 ul of Lipofectamine (Gibco). Incubate this solution at room temperature for 15-45 min.

Wash the cells 2× with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

IV. Ligand Binding Assay

Wash plates of transfected COS cells 1× with cold PBS (plus Ca/Mg)/1% goat serum.

Add 1 ml conditioned media neat and incubate 90 min at room temp.

Wash plates 3× with PBS (plus Ca/Mg). On the 4th wash, add 1 ml 50% methanol to 1 ml PBS. Then add 1 ml methanol. Evacuate and add 1 ml methanol.

Wash 1× with PBS. Wash 1X PBS/1% goat serum.

Add secondary antibody (1-to-2,000 anti-human Fc conjugated to alkaline phosphatase (Jackson Lab)) in PBS/1% goat serum. Incubate 30-40 mlin room ternp.

Wash 3× with PBS. Wash 1× alkaline phosphatase buffer (100 mM Tris-Cl, pH 9.5, 100 mM NaCl, 5 mM MgCl). Prepare alkaline phosphatase reagents: 4.5 ul/ml NBT and 3.5 ul/ml BCIP (Gibco) in alkaline phosphatase buffer.

Incubate 10-30 min, quench with 20 mM EDTA in PBS. Cells that have bound RGM are visible by the presence of a dark purple reaction product.

In parallel incubations, positive controls are provided by titrating RGM binding with serial dilutions of the mutant receptor conditioned medium.

V. Results: Binding of RGM to Neogenin

Cell expressing mammalian RGM were shown to bind Neogenin. No reactivity was observed with control COS cells or with receptor-expressing COS cells in the presence of the secondary antibody but in the absence of the RGM-Fc fusion.

Binding was observed to receptor-expression cells using a construct in which RGM is fused directly to alkaline phosphatase, for which a secondary antibody is not required. Neogenin deletion mutants titrate the RGM-receptor binding, serving as a positive control for inhibition assays.

Example 3

Comparison of axonal guidance phenotypes in Neogenin, DCC, Netrin, and RGM null mice.

In order to assess the functional role of the RGM/Neogenin system in neurological outcome after brain or spinal cord injury, studies in mice with targeted gene deletions are studied. These mice are created using mouse Embryonic Stem (ES) cells selected to contain disruptions of the endogenous genes of interest. The ES cells with gene disruptions is injected into mouse blastocysts to derive chimeric animals and then the targeted mutation are bred to homozygosity. In mice lacking Neogenin or RGM1 or RGM2 or RGM3 functional protein, various mouse models for human neurological disease are studied. For example, middle cerebral artery occlusion (MCAO) is created in mice using an intraluminal thread by standard methods. This MCAO produces a stroke in the brain and functional deficits in behavior. The recovery of mice from such injury in wild type and gene targeted lines is compared. The RGM/Neogenin interaction limits recovery from injury. Parallel studies of brain trauma and spinal cord traums are also made with mice lacking Neogenin or RGM1 or RGM2 or RGM3 function. Brain trauma is created by fluid percussion and spinal cord injury is created by either transection or by contusion. Improved recovery of mouse behavior after these traumatic lesions demonstrates the role of the RGM/Neogenin interaction in limiting recovery from CNS damage. Agents demonstrated to be inhibitory to the RGM/Neogenin interaction similarly improve recovery in wild-type mice exposed to brain trauma/spinal cord injury etc.

REFERENCES

1. Tessier-Lavigne, M. & Goodman, C. S. The molecular biology of axon guidance. *Science* 274, 1123-1133. (1996).
2. Yu, T. W. & Bargmann, C. I. Dynamic regulation of axon guidance. *Nat Neurosci* 4 Suppl, 1169-76 (2001).
3. Monnier, P. P. et al. RGM is a repulsive guidance molecule for retinal axons. *Nature* 419, 392-5 (2002).
4. Wang, H., Copeland, N. G., Gilbert, D. J., Jenkins, N. A. & Tessier-Lavigne, M. Netrin-3, a mouse homolog of human NTN2L, is highly expressed in sensory ganglia and shows differential binding to netrin receptors. *J Neurosci* 19,4938-47 (1999).
5. Feldheim, D. A. et al. Genetic analysis of ephrin-A2 and ephrin-A5 shows their requirement in multiple aspects of retinocollicular mapping. *Neuron* 25, 563-74 (2000).
6. Fazeli, A. et al. Phenotype of mice lacking functional Deleted in colorectal cancer (Dcc) gene. *Nature* 386, 796-804 (1997).
7. Serafini, T. et al. Netrin-1 is required for commissural axon guidance in the developing vertebrate nervous system. *Cell* 87, 1001-14 (1996).
8. Hong, K et al. A ligand-gated association between cytoplasmic domains of UNC5 and DCC family receptors converts netrin-induced growth cone attraction to repulsion. *Cell* 97, 927-41 (1999).
9. Geisbrecht, B. V., Dowd, K. A., Barfield, R. W., Longo, P. A. & Leahy, D. J. Netrin binds discrete subdomains of DCC and UNC5 and mediates interactions between DCC and heparin. *J Biol Chem* (2003).
10. Walter, J., Kern-Veits, B., Huf, J., Stolze, B. & Bonhoeffer, F. Recognition of position-specific properties of tectal cell membranes by retinal axons in vitro. *Development* 101, 685-96 (1987).
11. Walter, J., Henke-Fahle, S. & Bonhoeffer, F. Avoidance of posterior tectal membranes by temporal retinal axons. *Development* 101,909-13 (1987).
12. Ming, G. L. et al. cAMP-dependent growth cone guidance by netrin-1. *Neuron* 19, 1225-35 (1997).
13. Fournier, A. E., GrandPre, T. & Strittmatter, S. M. Identification of a receptor mediating Nogo-66 inhibition of axonal regeneration. *Nature* 409, 341-6 (2001).
14. Vielmetter, J., Stolze, B., Bonhoeffer, F. & Stuermer, C. A. In vitro assay to test differential substrate affinities of growing axons and migratory cells. *Exp Brain Res* 81,283-7 (1990).

We claim:

1. A method for identifying an agent which modulates the binding of a Repulsive Guidance Molecule (RGM) to a Neogenin, the method comprising the steps of: (a) forming a mixture comprising an isolated mammalian RGM and an isolated mammalian Neogenin, wherein the isolated mammalian Neogenin has the amino acid sequence of SEQ ID NO: 1; (b) incubating said mixture in the presence of an agent; and (c) detecting in the incubated mixture of step (b) the level of specific binding between said RGM and said Neogenin, wherein a difference in the detected level of specific binding of said RGM to said Neogenin in the presence of said agent relative to the level of specific binding in the absence of said agent indicates that said agent modulates the binding of said RGM to said Neogenin, wherein said RGM is RGM A or RGM B.

2. A method for monitoring the binding of a Repulsive Guidance Molecule (RGM), wherein said RGM is RGM A or RGM B to a Neogenin, the method comprising the steps of: (a) contacting a first protein comprising said RGM tagged with a visible stain or enzymatic signal, with a second protein which comprises the Neogenin, wherein said Neogenin has the amino acid sequence of SEQ ID NO: 1 and with a RGM A-specific antibody, or a RGM B specific antibody which will interfere in the binding between the tagged RGM A or RGM B and the Neogenin; (b) leaving the mixture for a time and under conditions where a domain of the RGM A or RGM B binds to a domain of the Neogenin; and (c) monitoring the binding of the first protein which comprises the tagged RGM, to the second protein which comprises the Neogenin, wherein a reduction in the visible stain or enzymatic signal indicates a reduction of tagged RGM binding to Neogenin due to the antibody interacting with said binding.

* * * * *

UNITED STATES PATENT AND TRADEMARK OFFICE

CERTIFICATE OF CORRECTION

PATENT NO. : 7,771,952 B2
APPLICATION NO. : 10/519132
DATED : August 10, 2010
INVENTOR(S) : Strittmatter et al.

It is certified that error appears in the above-identified patent and that said Letters Patent is hereby corrected as shown below:

In Front page, Assignee name error: “Abott” to read as --Abbott--

Column 38, line 6, claim 2: “RGM B specific antibody” to read as --RGM B-specific antibody--

Signed and Sealed this
Twenty-fourth Day of May, 2011

David J. Kappos
*Director of the United States Patent and Trademark Office*

SEQUENCE LISTING

```
<160> NUMBER OF SEQ ID NOS: 2

<210> SEQ ID NO 1
<211> LENGTH: 1445
```

-continued

```
<212> TYPE: PRT
<213> ORGANISM: Homo sapiens

<400> SEQUENCE: 1

Met Ala Ala Glu Arg Glu Ala Gly Arg Leu Leu Cys Thr Ser Ser Ser
1               5                   10                  15

Arg Arg Cys Cys Pro Pro Pro Pro Leu Leu Leu Leu Leu Pro Leu Leu
            20                  25                  30

Leu Leu Leu Gly Arg Pro Ala Ser Gly Ala Ala Ala Thr Lys Ser Gly
        35                  40                  45

Ser Pro Pro Gln Ser Ala Gly Ala Ser Val Arg Thr Phe Thr Pro Phe
    50                  55                  60

Tyr Phe Leu Val Glu Pro Val Asp Thr Leu Ser Val Arg Gly Ser Ser
65                  70                  75                  80

Val Ile Leu Asn Cys Ser Ala Tyr Ser Glu Pro Ser Pro Asn Ile Glu
                85                  90                  95

Trp Lys Lys Asp Gly Thr Phe Leu Asn Leu Glu Ser Asp Asp Arg Arg
            100                 105                 110

Gln Leu Leu Pro Asp Gly Ser Leu Phe Ile Ser Asn Val Val His Ser
        115                 120                 125

Lys His Asn Lys Pro Asp Glu Gly Phe Tyr Gln Cys Val Ala Thr Val
    130                 135                 140

Asp Asn Leu Gly Thr Ile Val Ser Arg Thr Ala Lys Leu Thr Val Ala
145                 150                 155                 160

Gly Leu Pro Arg Phe Thr Ser Gln Pro Glu Pro Ser Ser Val Tyr Val
                165                 170                 175

Gly Asn Ser Ala Ile Leu Asn Cys Glu Val Asn Ala Asp Leu Val Pro
            180                 185                 190

Phe Val Arg Trp Glu Gln Asn Arg Gln Pro Leu Leu Leu Asp Asp Arg
        195                 200                 205

Ile Val Lys Leu Pro Ser Gly Thr Leu Val Ile Ser Asn Ala Thr Glu
    210                 215                 220

Gly Asp Gly Gly Leu Tyr Arg Cys Ile Val Glu Ser Gly Gly Pro Pro
225                 230                 235                 240

Lys Phe Ser Asp Glu Ala Glu Leu Lys Val Leu Gln Asp Arg Glu Glu
                245                 250                 255

Ile Val Asp Leu Val Phe Leu Met Arg Pro Ser Ser Met Met Lys Val
            260                 265                 270

Thr Gly Gln Arg Ala Val Leu Pro Cys Val Val Ser Gly Leu Pro Ala
        275                 280                 285

Pro Val Val Arg Trp Met Lys Asn Glu Glu Val Leu Asp Thr Glu Ser
    290                 295                 300

Ser Gly Arg Leu Val Leu Leu Ala Gly Gly Gly Leu Glu Ile Ser Asp
305                 310                 315                 320

Val Thr Glu Asp Asp Ala Gly Thr Tyr Phe Cys Ile Ala Asp Asn Gly
                325                 330                 335

Asn Lys Thr Val Glu Ala Gln Ala Glu Leu Thr Val Gln Val Pro Pro
            340                 345                 350

Gly Phe Leu Lys Gln Pro Ala Asn Ile Tyr Ala His Glu Ser Met Asp
        355                 360                 365

Ile Val Phe Glu Cys Glu Val Thr Gly Lys Pro Thr Pro Thr Val Lys
    370                 375                 380

Trp Val Lys Asn Gly Asp Val Val Ile Pro Ser Asp Tyr Phe Lys Ile
385                 390                 395                 400
```

-continued

```
Val Lys Glu His Asn Leu Gln Val Leu Gly Leu Val Lys Ser Asp Glu
                405                 410                 415

Gly Phe Tyr Gln Cys Ile Ala Glu Asn Asp Val Gly Asn Ala Gln Ala
            420                 425                 430

Gly Ala Gln Leu Ile Ile Leu Glu His Ala Pro Ala Thr Thr Gly Pro
        435                 440                 445

Leu Pro Ser Ala Pro Arg Asp Val Val Ala Ser Leu Val Ser Thr Arg
    450                 455                 460

Phe Ile Lys Leu Thr Trp Arg Thr Pro Ala Ser Asp Pro His Gly Asp
465                 470                 475                 480

Asn Leu Thr Tyr Ser Val Phe Tyr Thr Lys Glu Gly Val Asp Arg Glu
                485                 490                 495

Arg Val Glu Asn Thr Ser Gln Pro Gly Glu Met Gln Val Thr Ile Gln
            500                 505                 510

Asn Leu Met Pro Ala Thr Val Tyr Ile Phe Lys Val Met Ala Gln Asn
        515                 520                 525

Lys His Gly Ser Gly Glu Ser Ser Ala Pro Leu Arg Val Glu Thr Gln
    530                 535                 540

Pro Glu Val Gln Leu Pro Gly Pro Ala Pro Asn Ile Arg Ala Tyr Ala
545                 550                 555                 560

Thr Ser Pro Thr Ser Ile Thr Val Thr Trp Glu Thr Pro Leu Ser Gly
                565                 570                 575

Asn Gly Glu Ile Gln Asn Tyr Lys Leu Tyr Tyr Met Glu Lys Gly Thr
            580                 585                 590

Asp Lys Glu Gln Asp Ile Asp Val Ser Ser His Ser Tyr Thr Ile Asn
        595                 600                 605

Gly Leu Lys Lys Tyr Thr Glu Tyr Ser Phe Arg Val Val Ala Tyr Asn
    610                 615                 620

Lys His Gly Pro Gly Val Ser Thr Gln Asp Val Ala Val Arg Thr Leu
625                 630                 635                 640

Ser Asp Val Pro Ser Ala Ala Pro Gln Asn Leu Ser Leu Glu Val Arg
                645                 650                 655

Asn Ser Lys Ser Ile Val Ile His Trp Gln Pro Pro Ser Ser Thr Thr
            660                 665                 670

Gln Asn Gly Gln Ile Thr Gly Tyr Lys Ile Arg Tyr Arg Lys Ala Ser
        675                 680                 685

Arg Lys Ser Asp Val Thr Glu Thr Leu Val Thr Gly Thr Gln Leu Ser
    690                 695                 700

Gln Leu Ile Glu Gly Leu Asp Arg Gly Thr Glu Tyr Asn Phe Arg Val
705                 710                 715                 720

Ala Ala Leu Thr Val Asn Gly Thr Gly Pro Ala Thr Asp Trp Leu Ser
                725                 730                 735

Ala Glu Thr Phe Glu Ser Asp Leu Asp Glu Thr Arg Val Pro Glu Val
            740                 745                 750

Pro Ser Ser Leu His Val Arg Pro Leu Val Thr Ser Ile Val Val Ser
        755                 760                 765

Trp Thr Pro Pro Glu Asn Gln Asn Ile Val Val Arg Gly Tyr Ala Ile
    770                 775                 780

Gly Tyr Gly Ile Gly Ser Pro His Ala Gln Thr Ile Lys Val Asp Tyr
785                 790                 795                 800

Lys Gln Arg Tyr Tyr Thr Ile Glu Asn Leu Asp Pro Ser Ser His Tyr
                805                 810                 815
```

-continued

```
Val Ile Thr Leu Lys Ala Phe Asn Asn Val Gly Glu Gly Ile Pro Leu
            820                 825                 830

Tyr Glu Ser Ala Val Thr Arg Pro His Thr Val Pro Asp Pro Thr Pro
        835                 840                 845

Met Met Pro Pro Val Gly Val Gln Ala Ser Ile Leu Ser His Asp Thr
    850                 855                 860

Ile Arg Ile Thr Trp Ala Asp Asn Ser Leu Pro Lys His Gln Lys Ile
865                 870                 875                 880

Thr Asp Ser Arg Tyr Tyr Thr Val Arg Trp Lys Thr Asn Ile Pro Ala
                885                 890                 895

Asn Thr Lys Tyr Lys Asn Ala Asn Ala Thr Thr Leu Ser Tyr Leu Val
            900                 905                 910

Thr Gly Leu Lys Pro Asn Thr Leu Tyr Glu Phe Ser Val Met Val Thr
        915                 920                 925

Lys Gly Arg Arg Ser Ser Thr Trp Ser Met Thr Ala His Gly Ala Thr
    930                 935                 940

Phe Glu Leu Val Pro Thr Ser Pro Pro Lys Asp Val Thr Val Val Ser
945                 950                 955                 960

Lys Glu Gly Lys Pro Arg Thr Ile Ile Val Asn Trp Gln Pro Pro Ser
                965                 970                 975

Glu Ala Asn Gly Lys Ile Thr Gly Tyr Ile Ile Tyr Tyr Ser Thr Asp
            980                 985                 990

Val Asn Ala Glu Ile His Asp Trp  Val Ile Glu Pro Val  Val Gly Asn
        995                 1000                 1005

Arg Leu  Thr His Gln Ile Gln  Glu Leu Thr Leu Asp  Thr Pro Tyr
    1010                 1015                 1020

Tyr Phe  Lys Ile Gln Ala Arg  Asn Ser Lys Gly Met  Gly Pro Met
    1025                 1030                 1035

Ser Glu  Ala Val Gln Phe Arg  Thr Pro Lys Ala Leu  Gly Ser Ala
    1040                 1045                 1050

Gly Lys  Gly Ser Arg Leu Pro  Asp Leu Gly Ser Asp  Tyr Lys Pro
    1055                 1060                 1065

Pro Met  Ser Gly Ser Asn Ser  Pro His Gly Ser Pro  Thr Ser Pro
    1070                 1075                 1080

Leu Asp  Ser Asn Met Leu Leu  Val Ile Ile Val Ser  Val Gly Val
    1085                 1090                 1095

Ile Thr  Ile Val Val Val Val  Val Ile Ala Val Phe  Cys Thr Arg
    1100                 1105                 1110

Arg Thr  Thr Ser His Gln Lys  Lys Lys Arg Ala Ala  Cys Lys Ser
    1115                 1120                 1125

Val Asn  Gly Ser His Lys Tyr  Lys Gly Asn Cys Lys  Asp Val Lys
    1130                 1135                 1140

Pro Pro  Asp Leu Trp Ile His  His Glu Arg Leu Glu  Leu Lys Pro
    1145                 1150                 1155

Ile Asp  Lys Ser Pro Asp Pro  Asn Pro Val Met Thr  Asp Thr Pro
    1160                 1165                 1170

Ile Pro  Arg Asn Ser Gln Asp  Ile Thr Pro Val Asp  Asn Ser Met
    1175                 1180                 1185

Asp Ser  Asn Ile His Gln Arg  Arg Asn Ser Tyr Arg  Gly His Glu
    1190                 1195                 1200

Ser Glu  Asp Ser Met Ser Thr  Leu Ala Gly Arg Arg  Gly Met Arg
    1205                 1210                 1215

Pro Lys  Met Met Met Pro Phe  Asp Ser Gln Pro Pro  Gln Pro Val
```

-continued

```
    1220                1225                1230

Ile Ser  Ala His Pro Ile His  Ser Leu Asp Asn Pro  His His His
    1235                1240                1245

Phe His  Ser Ser Ser Leu Ala  Ser Pro Ala Arg Ser  His Leu Tyr
    1250                1255                1260

His Pro  Ser Ser Pro Trp Pro  Ile Gly Thr Ser Met  Ser Leu Ser
    1265                1270                1275

Asp Arg  Ala Asn Ser Thr Glu  Ser Val Arg Asn Thr  Pro Ser Thr
    1280                1285                1290

Asp Thr  Met Pro Ala Ser Ser  Ser Gln Thr Cys Cys  Thr Asp His
    1295                1300                1305

Gln Asp  Pro Glu Gly Ala Thr  Ser Ser Ser Tyr Leu  Ala Ser Ser
    1310                1315                1320

Gln Glu  Glu Asp Ser Gly Gln  Ser Leu Pro Thr Ala  His Val Arg
    1325                1330                1335

Pro Ser  His Pro Leu Lys Ser  Phe Ala Val Pro Ala  Ile Pro Pro
    1340                1345                1350

Pro Gly  Pro Pro Leu Tyr Asp  Pro Ala Leu Pro Ser  Thr Pro Leu
    1355                1360                1365

Leu Ser  Gln Gln Ala Leu Asn  His His Ile His Ser  Val Lys Thr
    1370                1375                1380

Ala Ser  Ile Gly Thr Leu Gly  Arg Ser Arg Pro Pro  Met Pro Val
    1385                1390                1395

Val Val  Pro Ser Ala Pro Glu  Val Gln Glu Thr Thr  Arg Met Leu
    1400                1405                1410

Glu Asp  Ser Glu Ser Ser Tyr  Glu Pro Asp Glu Leu  Thr Lys Glu
    1415                1420                1425

Met Ala  His Leu Glu Gly Leu  Met Lys Asp Leu Asn  Ala Ile Thr
    1430                1435                1440

Thr Ala
    1445


<210> SEQ ID NO 2
<211> LENGTH: 5198
<212> TYPE: DNA
<213> ORGANISM: Homo sapiens

<400> SEQUENCE: 2

gggggccgcg cgggccgggc cgggccgggc tggagccgag ccctgcggcg cagagaccgg     60

ctgaggcgcg ctgagggaag ggcgcgagcg ctccgcggcg ctatcgccgc cgccgccgcc    120

gccactcgtg ggtagagat ggcggcggag cgcgaagccg ggcgactcct ctgcacctcc    180

tcctcccggc gctgctgtcc gccaccgccg ctgctgctgt tgctgccgct gctgctgctg    240

ctcggacgcc cggcgtccgg cgccgcggcc acgaagagcg gctccccgcc gcagtccgca    300

ggagccagtg ttcgaacatt cactccgttt tattttctgg tggagccgat agacaccctc    360

tcagttagag gctcttctgt tatattaaat tgctcggcat attctgagcc ctctccaaac    420

attgaatgga agaaagatgg gactttttta aacttagaat cagatgatcg acgccagcta    480

ctcccagatg gatctttatt catcagcaac gtggtgcatt ccaaacacaa taagcctgac    540

gaaggtttct atcagtgtgt agccactgtg gataatcttg gaaccattgt cagcagaaca    600

gccaagctca cagtagcagg tcttccaaga tttaccagcc aaccagaacc ttcttcagtc    660
```

-continued

```
tatgttggaa acagtgcaat tctgaattgt gaagttaatg cagatttggt cccatttgtt     720
aggtgggaac agaatcgaca gccccttctt ctagatgaca ggattgtcaa acttccaagt     780
ggaacactgg ttatcagcaa tgctactgaa ggagatgggg gactctaccg ctgcattgtt     840
gaaagtggtg ggccaccaaa gtttagtgac gaagctgaat tgaaagttct tcaagatcgt     900
gaggaaattg tagacttggt atttctgatg cgaccatttt ctatgatgaa agtcactggt     960
cagcgtgcag tgttgccatg tgttgtctca gggcttcctg ctccagtcgt tagatggatg    1020
aaaaacgaag aagtgcttga cacagaaagc tctggcaggt tggtcttgct agcaggaggt    1080
ggcttggaga tcagtgatgt cactgaggat gatgctggga cttatttttg catagctgat    1140
aatggaaata agacagttga agctcaggcg gagcttactg tgcaagtgcc acctggattc    1200
ttgaaacaac ctgctaacat atatgctcac gaatccatgg acattgtatt tgaatgtgaa    1260
gtcactggga agccaactcc aactgtgaag tgggtcaaga atggggatgt ggttatcccc    1320
agtgattact ttaaaattgt aaaggaacat aatcttcaag ttttgggtct ggtgaaatca    1380
gatgaagggt tctatcaatg cattgctgag aatgatgttg gaaatgcaca agctggagcc    1440
cagctgataa tccttgagca tgcaccagcc acaacgggac cactaccttc agctcctcga    1500
gacgtcgtgg cctccctggt ctctactcgc ttcattaaat tgacatggcg tacacctgca    1560
tcagaccctc atggagacaa tctcacctac tctgtgttct acaccaagga aggggttgat    1620
agggagcgtg ttgagaatac cagccagcca ggagagatgc aggtgactat tcaaaacttg    1680
atgccagcaa ctgtgtacat cttcaaagtt atggctcaaa ataagcatgg ctctggagaa    1740
agttcagctc ctcttcgagt agagacacag cctgaggttc agctccctgg cccagcacct    1800
aatatccgtg cttatgcaac gtcacctact tctatcactg tcacctggga aacaccgtta    1860
tctggcaatg gggaaattca aaattacaaa ttgtactaca tggaaaaagg aactgataaa    1920
gaacaggata ttgatgtttc aagtcactcc tacaccatta atggactgaa gaaatacaca    1980
gaatatagtt tccgagtggt ggcctacaat aaacatggtc ctggagtttc tacacaagat    2040
gttgctgttc gaacattatc agatgttccc agtgctgctc ctcagaatct gtccttagaa    2100
gtgagaaatt caaagagtat agtgatccac tggcagcccc cttcctcaac cacacaaaat    2160
gggcagataa ctggctacaa gattcgatat cgaaaggcct cccgaaaaag tgatgtcact    2220
gagaccttgg taactgggac acagctgtct cagctgattg aaggtcttga tcgggggaca    2280
gaatataact tccgagtcgc tgctctcaca gtcaatggta caggtccagc aactgattgg    2340
ctgtctgctg aaacttttga aagcgaccta gatgaaactc gtgttcctga agtgcccagc    2400
tctcttcatg tccgtccgct cgtcactagc attgtagtga gctggactcc tccagagaac    2460
cagaacattg tggtccgagg ttatgccatc ggttacggca ttggcagccc tcatgcccag    2520
accatcaaag tggactataa acaacgttat tacaccattg aaaacttgga tccaagctct    2580
cattacgtga ttaccttgaa agcatttaac aatgttggcg aaggcatccc cctttatgag    2640
agtgctgtga ccagacctca cacagtgcca gatcccactc ccatgatgcc accagtggga    2700
gttcaggctt ccattctgag tcacgacacc ataaggatta cctgggcaga caactccctg    2760
cccaaacacc agaagattac agactcccgc tactacacag tccggtggaa gaccaacatc    2820
ccagcaaaca cgaagtacaa gaatgcaaat gcaacgacgt taagctattt ggttactggt    2880
ttaaagccaa atacgctcta tgagttctct gtgatggtga ccaaaggcag aaggtcaagc    2940
acgtggagta tgacagctca tggcgctacc tttgaattag ttcctacttc tccacctaag    3000
```

-continued

```
gatgtgacag ttgtgagtaa ggaaggaaaa cctagaacca tcatagtgaa ctggcagcct   3060
ccctctgaag ctaacggcaa gattacaggt tacatcatct attacagcac ggatgtgaat   3120
gcagagatac atgactgggt tattgaacca gttgtgggaa acagactgac tcaccagatt   3180
caagagttaa cacttgatac gccatactac ttcaaaatcc aggcccggaa ctcaaagggc   3240
atggggccca tgtctgaagc tgtacagttc agaacaccta aagccttagg gtcagcagga   3300
aaaggaagcc gactaccaga cctgggatct gactacaaac ctccaatgag tggcagcaac   3360
agccctcacg ggagccccac ctcccctctg gacagcaaca tgctgctggt catcattgtc   3420
tctgttggcg tcatcactat cgtggtggtt gtggtcattg ctgtcttttg tacccggcgc   3480
accacctctc accagaaaaa gaaacgagct gcgtgcaaat cagtgaatgg ctcccataag   3540
tacaagggca attgcaaaga tgtgaagcct ccagacctat ggatccatca cgagagacta   3600
gagttgaagc ctattgacaa gtctccagat cctaaccctg tcatgactga tactccaatc   3660
cctcgaaact ctcaagatat cacaccagtg gacaattcca tggatagcaa tatccatcaa   3720
aggcggaatt catacagagg gcatgagtca gaggacagca tgtctacact ggctggaagg   3780
aggggaatga gaccaaaaat gatgatgccc tttgactctc agccacctca gcctgtgatt   3840
agtgcccatc ccatccattc cctcgataac cctcaccatc atttccactc cagcagcctc   3900
gcttctccag cccgcagtca tctctaccac ccaagcagcc catggcccat tggcacatcc   3960
atgtcccttt cagacagggc caattccaca gaatctgttc gaaatacccc cagcacggac   4020
accatgccag cgtcctcgtc tcagacgtgc tgcactgacc atcaggaccc tgagggtgct   4080
actagctcct cttacttggc cagctcccaa gaggaagact caggccagag tcttcccaca   4140
gcccatgtcc gcccttccca ccctctgaag agcttcgctg tgccagcaat cccacccccca   4200
ggacctcctc tctatgatcc tgcactgcca agcacaccat tactgtccca gcaagctctg   4260
aaccatcaca ttcactcagt gaaaacagcc tccatcggga cgttaggaag gagccggcct   4320
cctatgccag tggttgttcc gagtgcccct gaagtacagg agaccaccag gattctggaa   4380
gactccgaga gtagctatga accagatgag ctgaccaaag agatggccca cctggaagga   4440
ctaatgaagg acctaaatgc catcacaaca gcctgatgac cttcgcctgg acatgactcc   4500
aagcctgagt ctacaagtct cggaacttaa ccttgaaaac aaggaattgt acagagtacg   4560
agaggacagc acttgagagc aggagccagc aaaccagcca gtgcctccat gtggggttgg   4620
ctccaggcac agccacctgc cttctcctgg tcagcctgga ttacacttgt gtggaggcag   4680
cttccctttg cctgctgaga gcctgcagga ctgggcacta tgggccaaaa ttttgtgtcc   4740
agggaagagg caagaagtac gacctgcctt ttgctttgtg gtcagtggct tgtgtctttg   4800
tgctgcaact gcatcacttt tatggagtgt agacattggc atttatgtac aattttgtgt   4860
cctattttat tttaccttaa aacactatca gaagccaagg gagtctgtga tgttctctca   4920
agcagttgac acttgactgt ggttccagtt acttacggaa agtcatcaac agtgaggttg   4980
tttgacacca ctgacaggca ttggcttgtt gtgggtttca tttttattct taattctgag   5040
acattgcatc ctctgccagc tgttaatcca tcactttgag gggaggacat gttgcattgc   5100
tgtttgtaag ctttttttatt attttttttat tataattatt aaaggcctga ctttctcctc   5160
tcaaaaaaaa aaaaaaaaaa aaaaaaaaaa aaaaaaaa                           5198
```